(12) United States Patent
Xu et al.

(10) Patent No.: US 12,411,141 B2
(45) Date of Patent: Sep. 9, 2025

(54) LC-MS METHODS FOR ANTIBODY ISOTYPING AND QUANTIFICATION

(71) Applicant: Regeneron Pharmaceuticals, Inc., Tarrytown, NY (US)

(72) Inventors: Xiaobin Xu, Old Greenwich, CT (US); Xiaoxiao Huang, Briarcliff Manor, NY (US); Haibo Qiu, Hartsdale, NY (US); Ning Li, New Canaan, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 469 days.

(21) Appl. No.: 17/022,942

(22) Filed: Sep. 16, 2020

(65) Prior Publication Data

US 2021/0080471 A1    Mar. 18, 2021

Related U.S. Application Data

(60) Provisional application No. 62/901,037, filed on Sep. 16, 2019, provisional application No. 63/064,868, filed on Aug. 12, 2020.

(51) Int. Cl.
*G01N 33/68* (2006.01)
*G01N 30/72* (2006.01)
(Continued)

(52) U.S. Cl.
CPC ..... *G01N 33/6854* (2013.01); *G01N 30/7233* (2013.01); *H01J 49/0031* (2013.01);
(Continued)

(58) Field of Classification Search
None
See application file for complete search history.

(56) References Cited

U.S. PATENT DOCUMENTS

2012/0263651 A1    10/2012  Widen et al.
2012/0315645 A1*   12/2012  Kaur ............... G01N 33/6854
                                                            435/7.1
(Continued)

FOREIGN PATENT DOCUMENTS

JP      2004509323 A        3/2004
JP      2014509853 A        4/2014
WO      WO-2012177755 A1 *  12/2012  ........... G01N 27/745

OTHER PUBLICATIONS

Chen et al. "Development of Immunocapture-LC/MS assay for simultaneous ADA isotyping and semiquantitation". J Immunol Res. 7682472 (2016) (Year: 2016).*
(Continued)

*Primary Examiner* — Christopher L Chin
(74) *Attorney, Agent, or Firm* — Bookoff McAndrews, PLLC

(57) ABSTRACT

The present invention provides methods and systems for isotyping and quantification of antibodies based on immunocapture and/or Liquid Chromatography-Mass Spectrometry (LC-MS) analysis. These antibodies are induced by the administration of pharmaceutical products. The immunocapture method comprises contacting samples with a solid support, wherein the pharmaceutical product has been crosslinked directly to the solid support. The MS analysis includes conducting peptide mapping, selecting unique peptides and fragment ions to generate MRM (multiple reaction monitoring) transitions, optimizing collision energy, and determining a LLOQ (lower limit of quantification).

50 Claims, 20 Drawing Sheets

Specification includes a Sequence Listing.

(51) Int. Cl.
 H01J 49/00 (2006.01)
 H01J 49/16 (2006.01)
 H01J 49/42 (2006.01)
 G01N 30/02 (2006.01)

(52) U.S. Cl.
 CPC ............ H01J 49/165 (2013.01); H01J 49/42 (2013.01); *G01N 2030/027* (2013.01)

(56) References Cited

U.S. PATENT DOCUMENTS

2014/0194304 A1 7/2014 Shi et al.
2015/0031047 A1 1/2015 Alderman et al.

OTHER PUBLICATIONS

Amrani et al. ("Six-step workflow for the quantification of therapeutic monoclonal antibodies in biological matrices with liquid chromatography mass spectrometry". Analytica Chimica Acta 1080 22-34 (2019)) (Year: 2019).*

Diet induced ketosis increases monocarboxylate transporter (MCT1) levels in rat brain "Neurochemistry International". 38 519-527 (2001) (Year: 2001).*

Lonza, data sheet (2010) (Year: 2010).*

Lin-Zhi Chen et al: "Development of Immunocapture-LC/MS Assay for Simultaneous ADA Isotyping and Semiquantitation", Journal of Immunology Research, vol. 2016, Jan. 28, 2016 (Jan. 28, 2016), pp. 1-14.

El Amrani Mohsin et al: "Six-step workflow for the quantification of therapeutic monoclonal antibodies in biological matrices with liquid chromatography mass spectrometry—A tutorial", Analytica Chimica Acta, Elsevier, Amsterdam, NL, vol. 1080, Jun. 11, 2019 (Jun. 11, 2019), pp. 22-34.

Ming Yao et al: "LC-MS Differential 20,46 Analysis for Fast and Sensitive Determination of Biotransformation of Therapeutic Proteins", Drug Metabolism and Disposition, vol. 46, No. 4, Apr. 16, 2018 (Apr. 16, 2018), pp. 451-457.

International Search Report Date of Mailing Dec. 22, 2020, International Application No. PCT/US2020/051083, Filing Date Sep. 16, 2020.

* cited by examiner

SEQUENCE LISTING

```
<160> NUMBER OF SEQ ID NOS: 20

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Pro Ser Val Phe Pro Leu Ala Pro Ser Ser Lys
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

```
Gly Leu Pro Ala Pro Ile Glu Lys
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Tyr Val Asp Gly Val Glu Val His Asn Ala Lys
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Leu Pro Ser Ser Ile Glu Lys
1               5

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ala Ser Gly Ala Thr Phe Thr Trp Thr Pro Ser Ser Gly Lys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Ala Ser Gly Ala Thr Phe Thr Trp Thr Pro Ser Ser Gly Lys
1               5                   10                  15

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Ser Val Phe Val Pro Pro Arg
1               5

<210> SEQ ID NO 8
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 8

Asp Phe Thr Pro Pro Thr Val Lys
1               5

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Pro Ser Val Phe Pro Leu Ala Pro Ser Ser Arg
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Pro Ser Val Phe Pro Leu Ala Ser Cys Ser Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Pro Ser Val Phe Pro Leu Val Ser Cys Ser Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Pro Ser Val Phe Pro Leu Ala Ser Ser Ser Arg
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Ile Glu Val Ser Trp Leu Arg
1               5
```

```
<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Pro Ser Gly Ala Thr Phe Thr Trp Thr Pro Ser Ser Gly Lys
1               5                   10                  15

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Leu Pro Ala Pro Ile Gln Lys
1               5

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Thr Ser Glu Ser Thr Ala Ala Leu Gly Cys Leu Val Lys
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Val Ser Val Leu Thr Val Thr His Gln Asp Trp Leu Asn Gly Lys
1               5                   10                  15

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Trp Leu Ser Gln Ser Val Phe Thr Cys Arg
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 19

Cys Thr Val Thr His Thr Asp Leu Pro Ser Pro Leu Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Phe Ser Pro Glu Asp Val Leu Val Arg
1               5                   10
```

LC-MS METHODS FOR ANTIBODY ISOTYPING AND QUANTIFICATION

FIELD

The present invention generally pertains to methods and systems for isotyping and quantification of antibodies which are induced by the administration of pharmaceutical products. These methods and systems are based on immunocapture and/or liquid chromatography-mass spectrometry analysis.

SEQUENCE LISTING

The instant application contains a Sequence Listing which has been filed electronically in ASCII (.TXT) format and is hereby incorporated by reference in its entirety. The ASCII copy was created on Mar. 3, 2025, is named "00166-0228-02000_SL.txt", and is 5,252 bytes in size.

BACKGROUND

There are concerns of drug efficacy and patient safety due to the presence of antibodies which are induced by the administration of pharmaceutical products, for example, the induction of anti-drug antibodies (ADAs), since the ADAs can contribute to some clinical consequences, such as reducing drug efficacy, cross-reacting to endogenous proteins, or altering the pharmacokinetics of therapeutic proteins. FDA recommends adoption of a risk-based approach for evaluating and mitigating immune responses regarding adverse immunologically related responses associated with therapeutic protein products that affect their safety and efficacy. (Guidance for Industry: Immunogenicity Assessment for Therapeutic Protein Products, August 2014, U.S. Department of Health and Human Services, Food and Drug Administration)

The prescribing information and FDA's clinical pharmacology review of 121 FDA approved biologics were reviewed for evaluating and reporting immunogenicity data, including monoclonal antibodies, enzyme products, cytokines, growth factors and toxins. The highest frequency of reporting was for immunogenicity incidences. The clinical significance of ADAs was unknown. Overall, there was a striking concordance between an increase in systemic clearance of products and a reduction of efficacy associated with ADAs. (Wang et al., Evaluating and Reporting the Immunogenicity Impacts for Biological Products—a Clinical Pharmacology Perspective. The AAPS Journal. 2016; 18(2): 395-403)

The biological complexity of immune responses presents challenges to quantifying the impact of ADAs on pharmacokinetics, since pharmacokinetic exposure can be more sensitive than efficacy endpoints for evaluating ADA effects.

It will be appreciated that a need exists for methods to characterize ADAs, such as determining the isotypes of ADAs and further quantifying the presence of ADAs. These methods can provide valuable information regarding immunogenicity impacts in clinical pharmacology relevant to pharmacokinetics, efficacy, and safety for drug administrations, such as the administration of biologics.

SUMMARY

The immunogenicity incidences of protein pharmaceutical products have led to an increasing demand for characterizing the presence of antibodies which are induced by the administration of protein pharmaceutical products, for example, anti-drug antibodies (ADAs). The characterization data of ADAs can provide the understanding of immunogenicity of protein pharmaceutical products for enhancing drug safety.

Exemplary embodiments disclosed herein satisfy the aforementioned demands by providing methods and systems for characterizing, identifying and/or quantifying antibodies which are induced by the administration of pharmaceutical products. The methods and systems of the present application provide isotyping and quantification of ADAs using immunocapture and/or Liquid Chromatography-Mass Spectrometry (LC-MS) methods.

This disclosure, at least in part, provides a method of identifying at least one peptide or protein in a sample, comprising: contacting the sample to a solid support, wherein at least one pharmaceutical product has been attached to the solid support; washing the solid support using at least one mobile phase solution to provide at least one eluent; isolating the at least one peptide or protein from the eluent; treating the isolated peptide or protein with a denaturation solution and/or an enzymatic digestion reaction to generate components of the isolated peptide or protein; identifying the components of the isolated peptide or protein using a mass spectrometer.

In some exemplary embodiments, the method of identifying at least one peptide or protein in a sample is capable of determining an isotype or subclass of the isolated peptide or protein.

In some exemplary embodiments, the method of identifying at least one peptide or protein in a sample is capable of quantifying the isolated peptide or protein using a mass spectrometer.

In other exemplary embodiments, the pharmaceutical product in the method of the present application can be a drug, a chemical compound, a nucleic acid, a toxin, a peptide, a protein, a fusion protein, an antibody, an antibody fragment, a Fab region of an antibody, an antibody-drug conjugate, or a protein pharmaceutical product.

In some aspects, the at least one peptide or protein in the method of the present application can be an antibody that selectively binds to the pharmaceutical product attached to the solid support.

In some aspects, when the at least one peptide or protein in the method of the present application can be a human antibody, the isotype of the human antibody can be IgG1, IgG2, IgG3, IgG4, IgA1, IgA2, IgM, or IgE.

In other aspects, when the at least one peptide or protein in the method of the present application can be a mammalian antibody, the isotype of the mammalian antibody can be IgG1, IgG2, IgG3, IgG4, IgM, or IgA.

In yet other aspects, when the at least one peptide or protein in the method of the present application can be a human antibody, an amino acid sequence of the component of the isolated peptide or protein can be GPSVFPLAPSSK (SEQ ID NO: 1), GLPAPIEK (SEQ ID NO: 2), WYVDGVEVHNAK (SEQ ID NO: 3), GLPSSIEK (SEQ ID NO: 4), DASGVTFTWTPSSGK (SEQ ID NO: 5), DASGATFTWTPSSGK (SEQ ID NO: 6), VSVFVPPR (SEQ ID NO: 7), or DFTPPTVK (SEQ ID NO: 8).

In other aspects, when the at least one peptide or protein in the method of the present application can be a mammalian antibody, an amino acid sequence of the component of the isolated peptide or protein can be GPSVFPLAPSSR (SEQ ID NO: 9), GPSVFPLASCSR (SEQ ID NO: 10), GPSVFPLVSCSR (SEQ ID NO: 11), GPSVFPLASSSR (SEQ ID NO: 12), QIEVSWLR (SEQ ID NO: 13), or DPSGATFTWTPSSGK (SEQ ID NO: 14).

In some exemplary embodiments, the sample in the method of the present application can be treated with a solution to reach a pH range of about 0.1-4.5 prior to contacting the solid support, wherein the solution comprises acetic acid.

In some exemplary embodiments, the sample in the method of the present application can be incubated with the solid support at room temperature for about 1 hour.

In some aspects, the sample in the method of the present application further comprises a salt and a surfactant.

In other aspects, the sample in the method of the present application further comprises BSA (bovine serum albumin), HEPES (4-(2-hydroxyethyl)-1-piperazineethanesulfonic acid), sodium chloride, EDTA (ethylenediaminetetraacetic acid) and Tween-20 (polysorbate 20), wherein the sample has a pH range of about 6-9.

In some exemplary embodiments, the solid support in the method of the present application can be washed using the at least one mobile phase solution that comprises a salt and a surfactant and at least another subsequent mobile phase solution that has a pH range of about 0.1 to 4.5.

In some aspects, the at least one mobile phase solution in the method of the present application comprises BSA (bovine serum albumin), HEPES (4-(2-hydroxyethyl)-1-piperazineethanesulfonic acid), sodium chloride, EDTA (ethylenediaminetetraacetic acid) and Tween-20 (polysorbate 20) and has a pH range of about 6-9.

In some exemplary embodiments, the denaturation solution in the method of the present application comprises about 5-10 M urea.

In some exemplary embodiments, the enzyme of the enzymatic digestion reaction in the method of the present application can be trypsin.

In some exemplary embodiments, the pharmaceutical product in the method of the present application can be attached to the solid support using primary amine-epoxy reaction or using biotin-streptavidin interaction, wherein the pharmaceutical product can be attached to the solid support through cross-linking using a lysine residue of the pharmaceutical product for the primary amine-epoxy reaction.

In some exemplary embodiments, the mass spectrometer in the method of the present application can be an electrospray ionization mass spectrometer, nano-electrospray ionization mass spectrometer, or a triple quadrupole mass spectrometer, wherein the mass spectrometer can be coupled to a liquid chromatography system.

In some aspects, the mass spectrometer in the method of the present application can be capable of performing LC-MS (liquid chromatography-mass spectrometry) or a LC-MRM-MS (liquid chromatography-multiple reaction monitoring-mass spectrometry) analyses.

In some exemplary embodiments, the component of the isolated peptide or protein in the method of the present application can be at least about 0.01 ng, at least about 0.1 ng, at least about 0.2 ng, or at least about 0.3 ng.

In some exemplary embodiments, the method of identifying at least one peptide or protein in a sample can be capable of quantifying the isolated peptide or protein using a mass spectrometer, wherein the method further comprises the steps of: conducting peptide mapping of the isolated peptide or protein, selecting unique peptides and fragment ions of the isolated peptide or protein to generate MRM (multiple reaction monitoring) transitions, selecting top two or top three transitions of the unique peptide, optimizing collision energy of the unique peptide, subsequently generating a calibration curve, and determining a LLOQ (lower limit of quantification) according to the calibration curve.

This disclosure, at least in part, provides a system for identifying or quantifying at least one peptide or protein in a sample, comprising: a solid support, wherein a pharmaceutical product has been attached to the solid support; at least one mobile phase solution for washing the solid support and capable of providing at least one eluent containing the at least one peptide or protein for isolating the at least one peptide or protein; a denaturation solution and/or an enzymatic digestion solution capable of generating components from the isolated peptide or protein; and a mass spectrometer capable of identifying or quantifying the components from the isolated peptide or protein.

In some aspects, the mass spectrometer in the system of the present application is capable of identifying or quantifying an isotype or subclass of the isolated peptide or protein.

In some exemplary embodiments, the pharmaceutical product in the system of the present application can be a drug, a chemical compound, a nucleic acid, a toxin, a peptide, a protein, a fusion protein, an antibody, an antibody fragment, a Fab region of an antibody, an antibody-drug conjugate, or a protein pharmaceutical product.

In some exemplary embodiments, the at least one peptide or protein in the system of the present application can be an antibody that selectively binds to the pharmaceutical product attached to the solid support.

In some aspects, when the at least one peptide or protein in the system of the present application can be a human antibody, the isotype of the human antibody can be IgG1, IgG2, IgG3, IgG4, IgA1, IgA2, IgM, or IgE.

In some aspects, when the at least one peptide or protein in the system of the present application can be a mammalian antibody, the isotype of the mammalian antibody can be IgG1, IgG2, IgG3, IgG4, IgM, or IgA.

In other aspects, when the at least one peptide or protein in the system of the present application can be a human antibody, an amino acid sequence of the component of the isolated peptide or protein can be GPSVFPLAPSSK (SEQ ID NO: 1), GLPAPIEK (SEQ ID NO: 2), WYVDGVEVHNAK (SEQ ID NO: 3), GLPSSIEK (SEQ ID NO: 4), DASGVTFTWTPSSGK (SEQ ID NO: 5), DASGATFTWTPSSGK (SEQ ID NO: 6), VSVFVPPR (SEQ ID NO: 7), or DFTPPTVK (SEQ ID NO: 8).

In yet other aspects, when the at least one peptide or protein in the system of the present application can be a mammalian antibody, an amino acid sequence of the component of the isolated peptide or protein can be GPSVFPLAPSSR (SEQ ID NO: 9), GPSVFPLASCSR (SEQ ID NO: 10), GPSVFPLVSCSR (SEQ ID NO: 11), GPSVFPLASSSR (SEQ ID NO: 12), QIEVSWLR (SEQ ID NO: 13), or DPSGATFTWTPSSGK (SEQ ID NO: 14).

In some exemplary embodiments, the sample in the system of the present application can be treated with a solution to reach a pH range of about 0.1-4.5 prior to contacting the solid support, wherein the solution comprises acetic acid.

In some aspects, the sample in the system of the present application can be incubated with the solid support at room temperature for about 1 hour.

In some aspects, the sample in the system of the present application further comprises a salt and a surfactant.

In other aspects, the sample in the system of the present application further comprises BSA (bovine serum albumin), HEPES (4-(2-hydroxyethyl)-1-piperazineethanesulfonic acid), sodium chloride, EDTA (ethylenediaminetetraacetic acid) and Tween-20 (polysorbate 20), wherein the sample has a pH range of about 6-9.

In some exemplary embodiments, the solid support in the system of the present application can washed using the at least one mobile phase solution that comprises a salt and a surfactant and at least another subsequent mobile phase solution that has a pH range of about 0.1 to 4.5.

In some aspects, the at least one mobile phase solution in the system of the present application comprises BSA (bovine serum albumin), HEPES (4-(2-hydroxyethyl)-1-piperazineethanesulfonic acid), sodium chloride, EDTA (ethylenediaminetetraacetic acid) and Tween-20 (polysorbate 20) and has a pH range of about 6-9.

In some exemplary embodiments, the denaturation solution in the system of the present application comprises about 5-10 M urea.

In some exemplary embodiments, the enzyme of the enzymatic digestion reaction in the system of the present application can be trypsin.

In some exemplary embodiments, the pharmaceutical product in the system of the present application can be attached to the solid support using primary amine-epoxy reaction or using biotin-streptavidin interaction, wherein the pharmaceutical product can be attached to the solid support through cross-linking using a lysine residue of the pharmaceutical product for the primary-epoxy reaction.

In some exemplary embodiments, the mass spectrometer in the system of the present application can be an electrospray ionization mass spectrometer, nano-electrospray ionization mass spectrometer, or a triple quadrupole mass spectrometer, wherein the mass spectrometer can be coupled to a liquid chromatography system.

In some aspects, the mass spectrometer in the system of the present application can be capable of performing LC-MS (liquid chromatography-mass spectrometry) or a LC-MRM-MS (liquid chromatography-multiple reaction monitoring-mass spectrometry) analyses.

In some exemplary embodiments, the system of identifying or quantifying at least one peptide or protein in a sample can be capable of: conducting peptide mapping of the isolated peptide or protein, selecting unique peptides and fragment ions of the isolated peptide or protein to generate MRM (multiple reaction monitoring) transitions, selecting top two or top three transitions of the unique peptide, optimizing collision energy of the unique peptide, subsequently generating a calibration curve, and determining a LLOQ (lower limit of quantification) according to the calibration curve.

These, and other, aspects of the invention will be better appreciated and understood when considered in conjunction with the following description and the accompanying drawings. The following description, while indicating various embodiments and numerous specific details thereof, can be given by way of illustration and not of limitation. Many substitutions, modifications, additions, or rearrangements may be made within the scope of the invention.

BRIEF DESCRIPTION OF THE DRAWINGS

FIG. 2A shows the peak area of product ions according to an exemplary embodiment. FIG. 2B shows the selected collision energy according to an exemplary embodiment.

FIG. 5A shows the use of drug A to capture ADAs without using a denaturation solution for dissolving the dried ADAs. FIG. 5B shows the use of drug A or drug B to capture ADAs in the presence of a denaturation solution for dissolving the dried ADAs.

FIG. 17A shows the quantification for monkey A according to an exemplary embodiment. FIG. 17B show the quantification for monkey B according to an exemplary embodiment.

DETAILED DESCRIPTION

Figure 1:
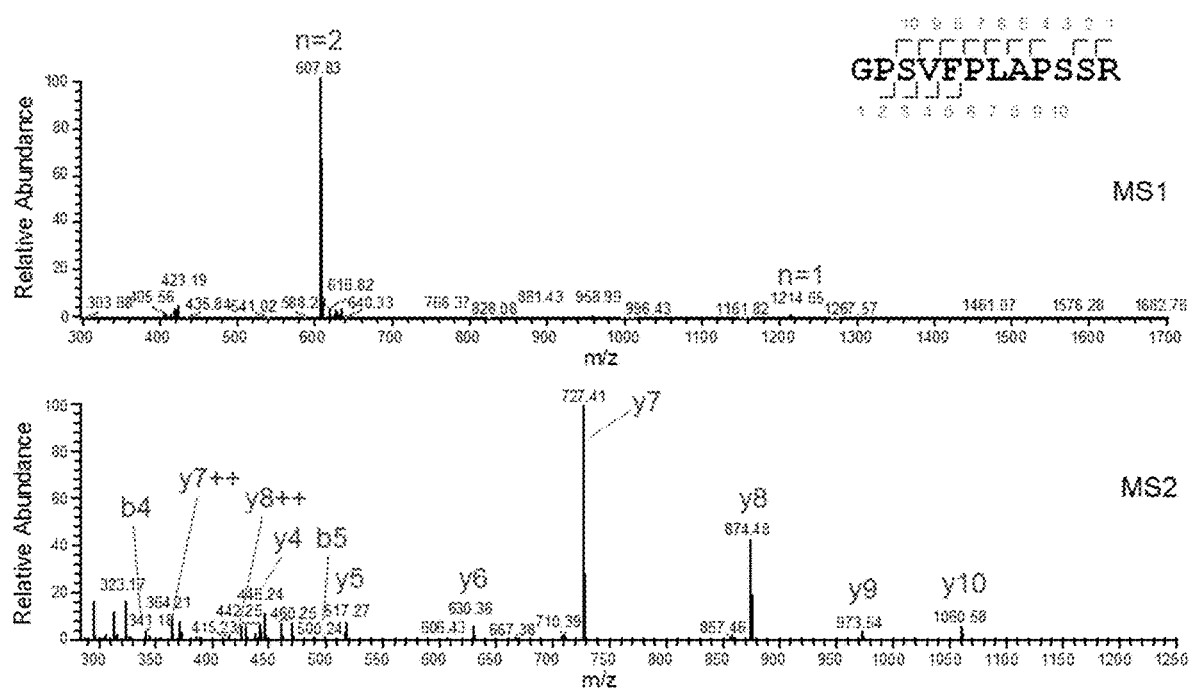
FIG. 1 shows the selection of product ions from the monkey IgG1 surrogate peptide according to an exemplary embodiment.

The increasing concerns of drug efficacy and patient safety due to immunogenicity incidences of protein pharmaceutical products have led to an increasing demand for characterizing the anti-drug antibodies (ADAs). The demands of characterizing ADAs are driven by, for example, the needs of understanding the impacts of ADAs on reducing the drug efficacy, cross-reacting to endogenous proteins, or altering the pharmacokinetics of pharmaceutical products. The characterization data of ADAs can provide valuable information regarding immunogenicity of pharmaceutical products, and therefore to enhance the safety for drug administrations.

This disclosure provides methods and systems to satisfy the aforementioned demands by providing methods and systems for characterizing, identifying and/or quantifying antibodies which are induced by the administration of pharmaceutical products. The methods and systems of the present application provide isotyping and quantification of ADAs using immunocapture and/or Liquid Chromatography-Mass Spectrometry (LC-MS) methods. These methods and systems can be applied in preclinical toxicology or pharmacokinetic studies to monitor ADAs over time after the administration of the pharmaceutical products by isotyping and quantification of ADAs.

There were reported incidences concerning the neutralizing activity of ADAs, such as immunogenicity impacts in clinical pharmacology relevant to pharmacokinetics, efficacy, and safety. The formation of ADAs during drug treatment may cause a decrease in drug concentration in a patient's body, which may contribute to the reduced efficacy. Various ADAs which are capable of binding to different sites of the drugs can be present in patient's bodies, such as neutralizing or non-neutralizing ADAs. Neutralizing ADAs are capable of binding to the active site of the drug molecule, such as the binding site in drug molecule for binding to the drug target, or the variable regions of an antibody drug. When the neutralizing ADA binds to the active site of a drug, it renders the drug inactive. The non-neutralizing ADA can be capable of binding to the non-active site of the drug molecule, such as the constant region or the scaffold of an antibody drug molecule. Even though the drug can be still active subjected to the binding of the non-neutralizing ADAs, the presence of non-neutralizing ADAs may contribute to certain changes in clinical pharmacology.

Immunogenicity refers to the propensity of the therapeutic product to generate immune responses to itself and to related proteins, such as inducing immunologically related adverse clinical events. Relevant immunogenicity information includes the induction of binding antibodies, the induction of neutralizing antibodies, altered pharmacokinetics, reduced efficacy, and safety concerns. However, the clinical significance of ADAs was unknown. In addition, the limited available data may preclude a determination of the effect of ADAs. ADAs may associate with a concordance between an increase in systemic clearance of pharmaceutical products and a reduction of efficacy. Some drug products had drug-sustaining ADAs which resulted in a reduced clearance possibly due to the formation of ADA-drug complex, such as ADA binding of the drug. (Wang et al., Evaluating and Reporting the Immunogenicity Impacts for Biological Products—a Clinical Pharmacology Perspective. The AAPS Journal. 2016; 18(2): 395-403)

Immunoglobulins are heterodimeric proteins composed of two heavy and two light chains. Immunoglobulin has variable domains that binds antigens and constant domains that specify effector functions. There are five main classes of heavy chain constant domains. Each class defines the isotypes of IgM, IgG, IgA, IgD, and IgE. IgG can be categorized into four subclasses, for example, IgG1, IgG2, IgG3, and IgG4. IgA can be categorized into IgA1 and IgA2. Different ADA isotypes can cause different immune responses.

The IgM isotype of ADAs can be generated by first drug exposure at 7 days with concentration of 1.5 mg/mL in serum. The function of IgM includes primary response and fixed complements. The monomer of IgM can serve as B-cell receptor. The IgG isotypes of ADAs can be generated by second drug exposure at 25-35 days with concentration of 0.5-9 mg/ml in serum. The function of IgG includes providing main blood antibody, neutralizing toxin, and opsonization. The IgA isotypes of ADAs have concentration of 0.5-3 mg/ml in serum. IgA can be secreted into mucus, tears and saliva. The IgE isotype of ADAs has concentration of 0.05 mg/ml in serum. IgE provides allergy and anti-parasitic activities. IgD isotype can proved B-cell receptor. (Schroder W H, Cavacini L. Structure and Function of Immunoglobulins. J Allergy Clin Immunol. 2010; 125(202): S41-S52)

FDA recommends developing ADA isotyping assays to understand potential patient immune responses, particularly for the incidence of ADA induction and the implications of ADA responses for therapeutic protein product safety and efficacy. The useful characterization assays include isotyping, epitope mapping, and assessing cross-reactivity to discriminate between antibody isotypes. (FDA Guidance for Industry: Assay Development and Validation for Immunogenicity Testing of Therapeutic Protein Products, draft, 2016)

In some exemplary embodiments, methods and systems are provided for isotyping and quantification of ADAs using immunocapture and Liquid Chromatography-Mass Spectrometry (LC-MS) methods. They satisfy the long felt needs of characterizing the antibodies induced by the administration of drugs or protein pharmaceutical products, which can be used to study preclinical or clinical toxicology and pharmacokinetics.

In some exemplary embodiments, an immunocapture method is coupled with LC-MS assays to isotype and quantify ADAs. The immunocapture method includes a step of using acid dissociation to treat a serum sample containing ADAs, wherein an acidic solution is added to the serum sample to prevent the aggregation or binding among the components in serum sample, such as the endogenous serum antibodies, protein pharmaceutical products, the antibody drug, pre-existing drugs or the ADAs. The acid dissociation treatments of the serum samples provide excellent advantages of reducing background noises for the later LC-MS analysis. Subsequently the ADAs in serum sample are captured by a pharmaceutical product which can be conjugated to a solid support, for example, drug conjugated beads or drug-beads, wherein the ADAs can selectively bind to the pharmaceutical product, wherein the pharmaceutical product can be a drug which induced the ADAs after the administration of the drug.

In some aspects, the ADAs are captured by drug conjugated beads through the incubation of drug conjugated beads and the serum samples containing ADA. Later, the beads are isolated, such as using a magnet to isolate drug conjugated magnetic beads. The isolated beads are washed. An elution step is followed to isolate the ADAs. The isolated ADAs are subject to an enzymatic digestion, such as a trypsin digestion. The unique peptides of each ADA isotype/subclass are identified and quantified using LC-MS or LC-MRM-MS (liquid chromatography-multiple reaction monitoring-mass spectrometry) methods.

In some exemplary embodiments, immunocapture methods for isolating ADAs from monkey or human serum samples are developed, including optimizing immunocapture to increase recovery rate of ADAs, minimizing background noises caused by nonspecific interactions, generating standard curves for quantification, and determining lower limit of quantification (LLOQ).

In some exemplary embodiments, a LC-MRM-MS method for ADA isotyping and quantification can be developed, including selecting a unique surrogate peptide for each isotype or subclass of monkey or human antibodies, selecting quantifying and confirming peptides for MRM (multiple reaction monitoring) quantitation, developing a MRM method on the triple quadrupole mass spectrometer, and determining instrument detection limit.

In some exemplary embodiments, the isolated ADAs are subjected to enzymatic digestions to obtain a combination of peptides. The combination of peptides are analyzed by the developed LC-MS or LC-MRM-MS method for identifying and quantifying isotypes of ADAs. In some exemplary embodiments, the developed LC-MS or LC-MRM-MS method further comprises the steps of: selecting a unique surrogate peptide for each isotype, conducting peptide mapping, selecting peptides and fragment ions to generate MRM transitions, selecting top two or top three transitions of the unique peptide, optimizing collision energy of the unique peptide, subsequently generating a calibration curve, and determining instrument detection limit according to the calibration curve. In some aspects, the peptide mapping is performed on QE plus (Q Exactive™ Plus Orbitrap LC-MS/MS System from Thermo Fisher Scientific), and the selection of top two or top three transitions are performed on triple quadrupole mass spectrometer.

LC-MS based method can be used to identify and quantify the antibody isotypes in the present application and are performed at peptide levels for the consideration of assay sensitivity, including the steps of enzyme digestion and quantification of the target antibodies based on selected signature unique peptides derived from the target antibodies.

The methods or systems of the present application provide the advantages of generating data sets which allow consistent identification and precise quantification of the isotypes of ADA across multiple samples. In some exemplary embodiments, the method or system of the present application provides a MRM based method to reliably quantify isotypes of ADA in low abundance in complex mixtures. In MRM approaches, a predefined precursor ion and one of its fragments are selected by the two mass filters of a triple quadrupole instrument. A series of precursor and fragment ion pairs, for example, transitions, are generated and monitored over time. When a series of transitions is combined with the retention time of the targeted peptide, it can provide a definitive assay for precise quantification. It enables the quantification of a large number of peptides during a single LC-MS experiment.

Considering the limitations of existing methods, an effective and sensitive method for identification and quantification of ADAs has been developed using immunocapture and LC-MS based method.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

As used herein, the terms "include," "includes," and "including," are meant to be non-limiting and are understood to mean "comprise," "comprises," and "comprising," respectively.

In some exemplary embodiments, the disclosure provides a method of identifying and/or quantification at least one peptide or protein in a sample, comprising: contacting the sample to a solid support, wherein at least one pharmaceutical product has been attached to the solid support; washing the solid support using at least one mobile phase solution to provide at least one eluent; isolating the at least one peptide or protein from the eluent; treating the isolated peptide or protein with a denaturation solution and/or an enzymatic digestion reaction to generate components of the isolated peptide or protein; identifying the components of the isolated peptide or protein using a mass spectrometer.

As used herein, the term "peptide" or "protein" includes any amino acid polymer having covalently linked amide bonds. Proteins comprise one or more amino acid polymer chains, generally known in the art as "peptide" or "polypeptides". A protein may contain one or multiple polypeptides to form a single functioning biomolecule. In some exemplary embodiments, the protein can be an antibody, a bispecific antibody, a multispecific antibody, antibody fragment, monoclonal antibody, host-cell protein or combinations thereof.

As used herein, at least one "pharmaceutical product" includes an active ingredient which can be fully or partially biological in nature or which has pharmaceutical activity. In some exemplary embodiments, the pharmaceutical product can comprise a drug, a peptide, a protein, a fusion protein, an antibody, an antibody fragment, a Fab region of an antibody, an antibody-drug conjugate, a Fc region of an antibody, an enzyme product, a cytokine, a growth factor, a protein pharmaceutical product, a toxin, a nucleic acid, DNA, RNA, a chemical compound, a cell, a tissue, or any pharmaceutical ingredient which can be capable of inducing antibodies in a subject.

As used herein, a "denaturation solution" includes alkaline solution, acid solution, or solution containing urea, guanidinium chloride, oxidizing agents, reducing agents, or organic solvents.

In some exemplary embodiments, the pharmaceutical product of the present application can be a drug, a chemical compound, a nucleic acid, a toxin, a peptide, a protein, a fusion protein, an antibody, an antibody fragment, a Fab region of an antibody, an antibody-drug conjugate, or a protein pharmaceutical product.

As used herein, a "protein pharmaceutical product" includes an active ingredient which can be fully or partially biological in nature. In some exemplary embodiments, the protein pharmaceutical product can comprise a peptide, a protein, a fusion protein, an antibody, an antigen, vaccine, a peptide-drug conjugate, an antibody-drug conjugate, a protein-drug conjugate, cells, tissues, or combinations thereof. In some other exemplary embodiments, the protein pharmaceutical product can comprise a recombinant, engineered, modified, mutated, or truncated version of a peptide, a protein, a fusion protein, an antibody, an antigen, vaccine, a peptide-drug conjugate, an antibody-drug conjugate, a protein-drug conjugate, cells, tissues, or combinations thereof.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a Fc fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. An antibody fragment may be produced by various means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex.

As used herein, the term "antibody-drug conjugate", or "ADC" can refer to antibody attached to biologically active drug(s) by linker(s) with labile bond(s). An ADC can comprise several molecules of a biologically active drug (or the payload) which can be covalently linked to side chains of amino acid residues of an antibody (Siler Panowski et al., Site-specific antibody drug conjugates for cancer therapy, 6 mAbs 34-45 (2013)). An antibody used for an ADC can be capable of binding with sufficient affinity for selective accumulation and durable retention at a target site. Most ADCs can have Kd values in the nanomolar range. The payload can have potency in the nanomolar/picomolar range and can be capable of reaching intracellular concentrations achievable following distribution of the ADC into target tissue. Finally, the linker that forms the connection between the payload and the antibody can be capable of being sufficiently stable in circulation to take advantage of the pharmacokinetic properties of the antibody moiety (e.g., long half-life) and to allow the payload to remain attached to the antibody as it distributes into tissues, yet should allow for efficient release of the biologically active drug once the ADC can be taken up into target cells. The linker can be: those that are non-cleavable during cellular processing and those that are cleavable once the ADC has reached the target site. With non-cleavable linkers, the biologically active drug released within the call includes the payload and all elements of the linker still attached to an amino acid residue of the antibody, typically a lysine or cysteine residue, following complete proteolytic degradation of the ADC within the lysosome. Cleavable linkers are those whose structure includes a site of cleavage between the payload and the amino acid attachment site on the antibody. Cleavage mechanisms can include hydrolysis of acid-labile bonds in acidic intracellular compartments, enzymatic cleavage of amide or ester bonds by an intracellular protease or esterase, and reductive cleavage of disulfide bonds by the reducing environment inside cells.

In some aspects, the at least one peptide or protein in the sample of the present application can be an antibody that selectively binds to the pharmaceutical product attached to the solid support.

As used herein, an "antibody" is intended to refer to immunoglobulin molecules consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has of a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL can be composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" is inclusive of, but not limited to, those that are prepared, expressed, created or isolated by recombinant means, such as antibodies isolated from a host cell transfected to express the antibody. An IgG comprises a subset of antibodies.

In some aspects, the method or system of the present application can be used to identify and quantify at least one peptide or protein in a sample, and the method further comprises the steps of: conducting peptide mapping of the isolated peptide or protein, selecting unique peptides and fragment ions of the isolated peptide or protein to generate MRM (multiple reaction monitoring) transitions, selecting top two or top three transitions of the unique peptide, optimizing collision energy of the unique peptide, subsequently generating a calibration curve, and determining a LLOQ (lower limit of quantification) according to the calibration curve.

As used herein, "peptide mapping" refers to a technology for confirming a protein's primary structure, e.g., amino acid sequence. Peptide mapping can be used for identification, primary structural characterization, and quality assurance/quality control (QA/QC). The unknown protein of interest can be first cleaved into smaller peptides, whose absolute masses can be accurately measured with a mass spectrometer such as coupling a liquid chromatography with tandem mass spectrometry (LC-MS/MS)-based peptide mapping platform for confirmation of protein primary structure.

In some aspects, the mass spectrometer in the method or system of the present application can be an electrospray ionization mass spectrometer, nano-electrospray ionization mass spectrometer, or a triple quadrupole mass spectrometer, wherein the mass spectrometer can be coupled to a liquid chromatography system, wherein the mass spectrometer is capable of performing LC-MS (liquid chromatography-mass spectrometry) or a LC-MRM-MS (liquid chromatography-multiple reaction monitoring-mass spectrometry) analyses.

As used herein, a "mass spectrometer" includes a device capable of identifying specific molecular species and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends heavily on the application.

As used herein, the term liquid "chromatography" refers to a process in which a chemical mixture carried by a liquid or gas can be separated into components as a result of differential distribution of the chemical entities as they flow around or over a stationary liquid or solid phase. Non-limiting examples of chromatography include traditional reversed-phased (RP), ion exchange (IEX), mixed mode chromatography and normal phase chromatography (NP).

As used herein, the term "electrospray ionization" or "ESI" refers to the process of spray ionization in which either cations or anions in solution are transferred to the gas phase via formation and desolvation at atmospheric pressure of a stream of highly charged droplets that result from applying a potential difference between the tip of the electrospray needle containing the solution and a counter electrode. There are generally three major steps in the production of gas-phase ions from electrolyte ions in solution. These are: (a) production of charged droplets at the ES infusion tip; (b) shrinkage of charged droplets by solvent evaporation and repeated droplet disintegrations leading to small highly charged droplets capable of producing gas-phase ions; and (c) the mechanism by which gas-phase ions are produced from very small and highly charged droplets. Stages (a)-(c) generally occur in the atmospheric pressure region of the apparatus. In some exemplary embodiments, the electrospray ionization mass spectrometer can be a nano-electrospray ionization mass spectrometer.

As used herein, the term "triple quadruple mass spectrometer" refers to a tandem mass spectrometer consisting of two quadrupole mass analyzers in series, with a (non-mass-resolving) radio frequency (RF), only quadrupole between them to act as a cell for collision-induced dissociation. In a triple quadrupole mass spectrometer, a peptide sample is injected onto an LC coupled with a MS instrument. The first quadrupole can be used as a mass filter to isolate peptides with a targeted m/z. The second quadrupole serves as a collision cell to break the peptide into fragments. The third quadrupole serves as a second mass filter for specified m/z fragments from the initial parent peptide. As used herein, the term "tandem mass spectrometry" includes a technique where structural information on sample molecules can be obtained by using multiple stages of mass selection and mass separation. A prerequisite is that the sample molecules can be transferred into gas phase and ionized intact and that they can be induced to fall apart in some predictable and controllable fashion after the first mass selection step. Multistage MS/MS, or $MS^n$, can be performed by first selecting and isolating a precursor ion ($MS^2$), fragmenting it, isolating a primary fragment ion ($MS^3$), fragmenting it, isolating a secondary fragment ($MS^4$), and so on as long as one can obtain meaningful information or the fragment ion signal can be detectable. Tandem MS have been successfully performed with a wide variety of analyzer combinations. What analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time mass spectrometer ions produced in the ion source can be trapped, isolated, fragmented, and m/z separated in the same physical device.

The peptides identified by the mass spectrometer can be used as surrogate representatives of the intact protein and their post-translational modifications. They can be used for protein characterization by correlating experimental and theoretical MS/MS data, the latter generated from possible peptides in a protein sequence database. The characterization can include, but is not limited, to sequencing amino acids of the protein fragments, determining protein sequencing, determining protein de novo sequencing, locating post-translational modifications, or identifying post translational modifications, or comparability analysis, or combinations thereof.

In some exemplary embodiments, an isotype or subclass of the isolated peptide or protein is determined.

As used herein, the term "isotype" or "subclass" refers to different isotypes of immunoglobulines. Immunoglobulins are heterodimeric proteins composed of two heavy and two light chains. Immunoglobulin has variable domains that binds antigens and constant domains that specify effector functions. The Fc portion of the heavy chains defines the class of antibody, of which there are five in mammalians: IgG, IgA, IgM, IgD and IgE. The classes differ in their biological properties, otherwise known as effector functions, and their functional localization to ensure an appropriate immune response for a given antigen. There are five main classes of heavy chain constant domains. Each class defines the isotypes of IgM, IgG, IgA, IgD, and IgE. IgG can be categorized into four subclasses, e.g., IgG1, IgG2, IgG3, and IgG4. IgA can be categorized into IgA1 and IgA2. When the antibody can be a human antibody, an isotype of the human antibody can be IgG1, IgG2, IgG3, IgG4, IgA1, IgA2, IgM, or IgE. When the antibody is a monkey antibody, an isotype of the monkey antibody can be IgG1, IgG2, IgG3, IgG4, IgM, or IgA.

EXEMPLARY EMBODIMENTS

Embodiments disclosed herein provide compositions, methods, and systems for the identification and quantification of isotypes or subclass of antibodies using immunocapture and mass-spectrometry based method.

In some exemplary embodiments, the disclosure provides a method of identifying and/or quantifying at least one peptide or protein in a sample, comprising: contacting the sample to a solid support, wherein at least one pharmaceutical product has been attached to the solid support; washing the solid support using at least one mobile phase solution to provide at least one eluent; isolating the at least one peptide or protein from the eluent; treating the isolated peptide or protein with a denaturation solution and/or an enzymatic digestion reaction to generate components of the isolated peptide or protein; identifying the components of the isolated peptide or protein using a mass spectrometer.

In some aspects, the sample in the method or system of the present application can be treated with an acidic solution to reach a pH range of about 0.1-4.5 prior to contacting the solid support. In some exemplary embodiments, the acidic solution has a pH range of about 3.6, about 0.1-3.6, about 1.0-4.0, about 2.0-4.0, about 3.0-4.0, about 1.5-4, about 2.5-4, or about 3.5-4. In some aspects, the acidic solution comprises acetic acid, phosphoric acid, boric acid, citric acid, carbonic acid, hydrochloric acid, nitric acid, sulfuric acid, hydrofluoric acid, or oxalic acid.

In other aspects, the sample in the method or system of the present application can be incubated with the solid support at room temperature (ambient temperature) for about 1 hour, about 5-60 minutes, about 5 minutes, about 10 minute, about 20 minutes, about 30 minutes, about 40 minutes, about 50 minutes, about 0.5-6 hours, about 0.5-1.5 hours, about 1.5 hours, about 2 hours, about 3 hours, about 6 hours, about 12 hours, or overnight. In some exemplary embodiments, the sample in the method or system of the present application can be incubated with the solid support at about 4-30 degree C. for about 1 hour, about 5-60 minutes, about 5 minutes, about 10 minute, about 20 minutes, about 30 minutes, about 40 minutes, about 50 minutes, about 0.5-6 hours, about 0.5-1.5 hours, about 1.5 hours, about 2 hours, about 3 hours, about 6 hours, about 12 hours, or overnight. In some exemplary embodiments, the sample in the method or system of the present application can be incubated with the solid support at about 4 degree C. for about 1 hour, about 5-60 minutes, about 5 minutes, about 10 minute, about 20 minutes, about 30 minutes, about 40 minutes, about 50 minutes, about 0.5-6 hours, about 0.5-1.5 hours, about 1.5 hours, about 2 hours, about 3 hours, about 6 hours, about 12 hours, or overnight.

In some aspects, the solid support in the method or system of the present application can be beads, magnetic beads, chromatography resins, polymer, or chromatography matrix.

In other aspects, the sample in the method or system of the present application further comprises a salt and a surfactant. In yet other aspects, the sample in the method or system of the present application further comprises BSA (bovine serum albumin), HEPES (4-(2-hydroxyethyl)-1-piperazineethanesulfonic acid), sodium chloride, EDTA (ethylenediaminetetraacetic acid) and Tween-20 (polysorbate 20), wherein the sample has a pH range of about 6-9.

In some aspects, the solid support in the method or system of the present application can be washed using the at least one mobile phase solution that comprises a salt and a surfactant and at least another subsequent mobile phase solution that has a pH range of about 0.1 to 4.5. In other aspects, the at least one mobile phase solution in the method or system of the present application comprises BSA (bovine serum albumin), HEPES (4-(2-hydroxyethyl)-1-piperazineethanesulfonic acid), sodium chloride, EDTA (ethylenediaminetetraacetic acid) and Tween-20 (polysorbate 20) and has a pH range of about 6-9.

In some exemplary embodiments, the denaturation solution in the method or system of the present application comprises about 8 M, about 5-10 M, about 7-9 M, about 6-9 M, or about 3-10 M urea. In some aspects, the denaturation solution can be an alkaline solution or an acid solution. In other aspects, the denaturation solution comprises, urea, guanidinium chloride, oxidizing agents, reducing agents, or organic solvents.

In some exemplary embodiments, the component of the isolated peptide or protein in the method or system of the present application can be at least about 0.01 ng, at least about 0.1 ng, at least about 0.2 ng, or at least about 0.3 ng, about 0.01-1.0 ng, about 0.2-0.4 ng, about 0.2-0.5 ng, or about 0.2-0.6 ng.

In some exemplary embodiments, the disclosure provides a system for identifying or quantifying at least one peptide or protein in a sample, comprising: a solid support, wherein a pharmaceutical product has been attached to the solid support; at least one mobile phase solution for washing the solid support and capable of providing at least one eluent containing the at least one peptide or protein for isolating the at least one peptide or protein; a denaturation solution and/or an enzymatic digestion solution capable of generating components from the isolated peptide or protein; and a mass spectrometer capable of identifying or quantifying the components from the isolated peptide or protein. In some exemplary embodiments, the mass spectrometer of the system is capable of performing LC-MS (liquid chromatography-mass spectrometry) or a LC-MRM-MS (liquid chromatography-multiple reaction monitoring-mass spectrometry) analyses. In some exemplary embodiments, the system is capable of: conducting peptide mapping, selecting unique peptides and fragment ions to generate MRM (multiple reaction monitoring) transitions, selecting top two or top three transitions, optimizing collision energy, subsequently generating a calibration curve, and determining a LLOQ (lower limit of quantification) according to the calibration curve.

In some aspects, the LLOQ comprises limit of detection (LOD) or limit of quantification (LOQ). In other aspects, the LOD for identification or quantification of the peptide or protein in a sample can be about 40 ng/mL, about 10-80 ng/mL, about 20-50 ng/mL, about 30-60 ng/mL, or about 35-45 ng/mL. In other aspects, the LOQ for identification or quantification of the peptide or protein in a sample can be about 120 ng/mL, about 80-160 ng/mL, about 100-140 ng/mL, or about 110-130 ng/mL.

It is understood that the system is not limited to any of the aforesaid pharmaceutical products, peptides, proteins, antibodies, anti-drug antibodies, antigen-antibody complex, protein pharmaceutical products, chromatography column, or mass spectrometer.

The consecutive labeling of method steps as provided herein with numbers and/or letters is not meant to limit the method or any embodiments thereof to the particular indicated order.

Various publications, including patents, patent applications, published patent applications, accession numbers, technical articles and scholarly articles are cited throughout the specification. Each of these cited references is herein incorporated by reference, in its entirety and for all purposes, herein.

The disclosure will be more fully understood by reference to the following Examples, which are provided to describe the disclosure in greater detail. They are intended to illustrate and should not be construed as limiting the scope of the disclosure.

EXAMPLES

Materials and Reagents Preparation.
1.1 Antibody Drugs to Capture ADA.

Several antibody drugs were used to capture ADAs from human or monkey serum samples as listed in Table 1.

TABLE 1

Antibody drugs for capturing ADAs

| Antibody Drug | Isotype (human) | Antigen |
|---|---|---|
| Drug A | IgG4 | PD1 (Programmed cell death protein 1) |
| Drug B | IgG4 | INHBA (Inhibin, beta A chain) |
| Drug C | IgG4 | ANGPTL3 (Angiopoietin-related protein 3) |
| Drug D | IgG1 | PCSK9 (Proprotein convertase subtilisin/kexin type 9) |
| Drug E | IgG1 | RSV (respiratory syncytial virus) Fusion Protein |
| Drug F | Fab of IgG4 | PD1 (Programmed cell death protein 1) |
| Drug G | Fab of IgG4 | INHBA (Inhibin, beta A chain) |
| Drug H | Fab of IgG4 | ANGPTL3 (Angiopoietin-related protein 3) |
| Drug I | Fab of IgG1 | PCSK9 (Proprotein convertase subtilisin/kexin type 9) |
| Drug J | Fab of IgG1 | RSV (respiratory syncytial virus) Fusion Protein |

2.1. Conjugate Antibody Drugs to Magnetic Beads.

Two types of conjugation methods were used to incorporate an antibody drug to a solid support, such as a magnetic bead. In the first method, the antibody drug was biotinylated using a biotinylation kit, such as an EZ-Link SulfoN-HS-LC Biotinylation Kit. (Chen et al., Development of Immunocapture-LC/MS Assay for Simultaneous ADA Isotyping and Semiquantitation, Journal of Immunology Research, Volume 2016, Article ID 7682472, 14 pages; Roos et al., Detection of cynomolgus monkey anti-protein XYZ antibody using immunocapture-LC/MS, Journal of Applied Bioanalysis, October 2016, Vol 2, No. 4, page 117-128) The biotinylated drugs were subsequently bound to streptavidin coated magnetic beads. In the second method, antibody drugs were cross-linked directly to the magnetic beads using primary amine-epoxy reaction through a lysine residue of the drug. The biotinylated drugs or cross-linked drugs were used to capture and isolate ADAs in human or monkey serum samples. A magnet was used to remove the magnetic beads from the serum sample.

3.1 ADA Positive Control.

A monkey IgG1 monoclonal anti-human kappa light chain antibody was used as an ADA positive control, for example, ADA-Std, for developing the immunocapture and LC-MS assay for ADA isotyping and quantification. ADA-Std can bind to human IgG.

Instrument for peptide identification and quantification. The mass spectrometer for peptide identification or quantification is an electrospray ionization mass spectrometer or nano-electrospray ionization mass spectrometer. The mass spectrometer is coupled to a liquid chromatography system. The mass spectrometer is capable of performing LC-MS (liquid chromatography-mass spectrometry) or a LC-MRM-MS (liquid chromatography-multiple reaction monitoring-mass spectrometry) analyses. In some exemplary embodiments, the mass spectrometer is a triple quadrupole mass spectrometer.

Example 1. Select Unique Surrogate Peptides to Identify and Quantify the ADA Isotype The identification and quantification of isotypes of ADAs by LC-MS were based on the unique surrogate peptides of ADAs rather than their whole molecules in considering the sensitivity of detection. Each ADA yields a combination of peptides upon tryptic digestion. Only a few representative peptides per ADA are targeted to infer the presence of a ADA and to determine the quantification of isotypes. (V. Lange, P. Picotti, B. Domon, and R. Aebersold, Selected reaction monitoring for quantitative proteomics: a tutorial, Molecular Systems Biology, vol. 4, article 222, 2008)

The quantitative measurement relies on the existence of a quantitative relationship between ADA and its surrogate peptide by identifying proper peptides that were unique to each antibody isotype. In order to select a suitable surrogate peptide for each antibody isotype, the surrogate peptide of each isotype should come from the constant region of the antibody. ADAs of the same isotype have different forms in terms of amino acid sequence in the variable regions, however they have the same constant region. In addition, the selected surrogate peptide is unique to each ADA isotype and should not be formed in any other isotypes. (Chen et al., Development of Immunocapture-LC/MS Assay for Simultaneous ADA Isotyping and Semiquantitation, Journal of Immunology Research, Volume 2016, Article ID 7682472, 14 pages) Furthermore, the surrogate peptides should not contain the amino acids of ADA allotype polymorphic residues (M.-P. Lefranc and G. Lefranc, Human Gm, Km, and Am allotypes and their molecular characterization: a remarkable demonstration of polymorphism, Methods in Molecular Biology, vol. 882, pp. 635-680, 2012). Since many isotypes share the same light chains (κ and λ), light chains were excluded from the surrogate peptide selection.

There are several considerations regarding the selection of surrogate peptides. Avoid peptides containing methionine which have the tendency of oxidation. Avoid peptide sequences containing arginine-arginine (RR) and lysine-lysine (KK), which can yield inconsistent tryptic digestion. Peptide sequences containing arginine-proline (RP) and lysine-proline (KP) are not preferable, since they are difficult to break down by digestion. The preferable peptide length is between 6 and 20 amino acids to minimize the number of ionization charge states, achieve efficient MS/MS fragmentation and high sensitivity, and obtain desirable chromatographic retention. It is also preferable to avoid peptide sequences containing glycosylation sites. (S. T. Wu, Z. Ouyang, T. V. Olah, and M. Jemal, A strategy for liquid chromatography/tandem mass spectrometry based quantitation of pegylated protein drugs in plasma using plasma protein precipitation with water-miscible organic solvents and subsequent trypsin digestion to generate surrogate peptides for detection, Rapid Communications in Mass Spectrometry, vol. 25, no. 2, pp. 281-290, 2011)

For the identification of unique surrogate peptides for each antibody isotype, the amino acid sequence alignments of IgG subclasses were performed. These sequences were subjected to the prediction based on in silico trypsin digestion to identify unique peptides.

Immunoglobulin solution was enzymatically digested and the resulting tryptic peptides were assayed and screened by LC-MS using information-dependent acquisition (IDA) method. The IDA setup consisted of MRM survey scan for the formation of tryptic peptides based on in silico prediction, followed by enhanced product ion scans to confirm peptide identity. Peptide separation was achieved with chromatography methods. The tryptic peptides with good LC-MS sensitivity were further evaluated. The specific peptides were identified by interpreting in silico tryptic peptides from each antibody isotype. The top 1-3 most sensitive peptides for each ADA isotype were selected as unique peptide candidates and carried on for further method development. Upon collision activation in MS/MS, the multiple charged parent ions fragmented into single charged b-ions and y-ions and the most sensitive y-ions were selected.

Figure 2A:
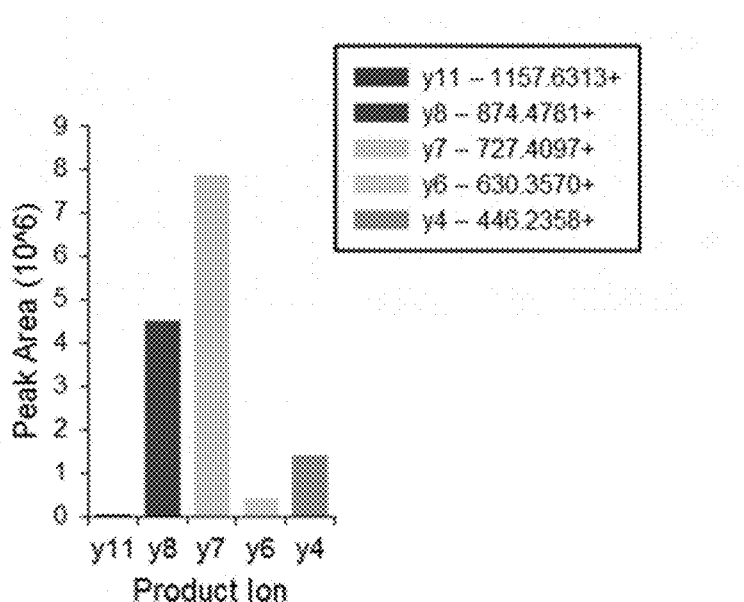
FIGS. 2A and 2B show the selection of top 2 transitions from the monkey IgG1 surrogate peptide and optimization of collision energy according to an exemplary embodiment.
Figure 2B:
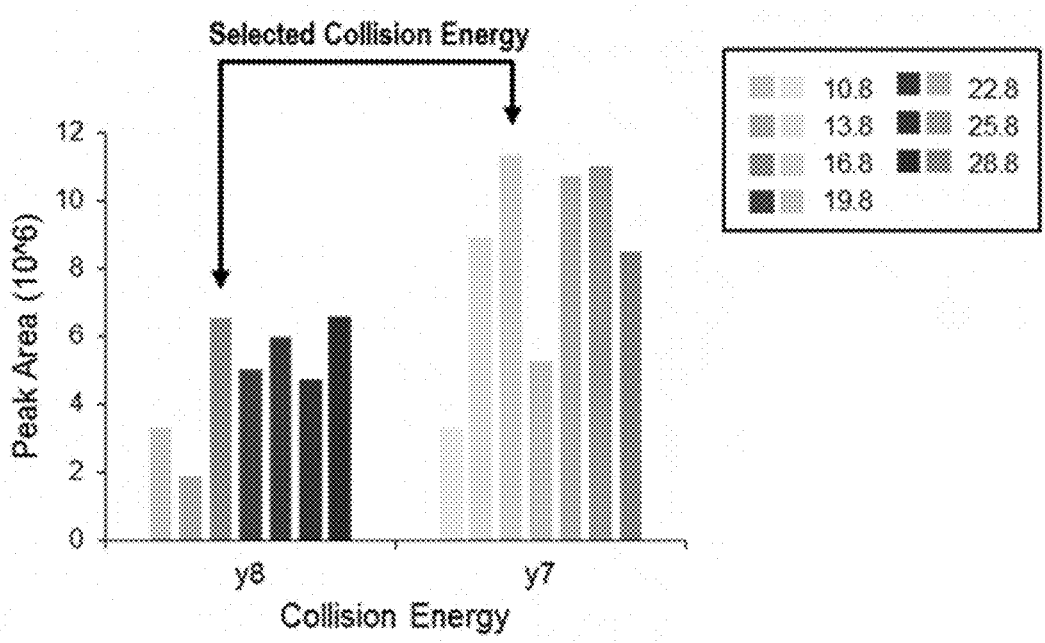

Specific product ions were selected for surrogate peptides. FIG. 1 shows the selection of product ions from the monkey IgG1 surrogate peptide. FIG. 2 and Table 2 shows the selection of top two transitions from the monkey IgG1 surrogate peptide and optimization of collision energy. FIG. 2A shows the peak area of product ions. FIG. 2B shows the selected collision energy.

Table 2

Top two transitions of the Monkey IgG1 surrogate peptide with product ion and collision energy

| Isotype | Peptide | Precursor | Product Ion | Ion Name | Collision Energy |
|---|---|---|---|---|---|
| Monkey IgG1 | GPSVFPLAPSSR (SEQ ID NO: 9) | 607.8300 | 727.4097 | y7 | 16.8 |
| | | 607.8300 | 874.4781 | y8 | 16.8 |

For the human antibody, the amino acid sequence of the unique surrogate peptide for identifying antibody isotype is GPSVFPLAPSSK (SEQ ID NO: 1) for IgG1, GLPAPIEK (SEQ ID NO: 2) for IgG2, WYVDGVEVHNAK (SEQ ID NO: 3) for IgG3, GLPSSIEK (SEQ ID NO: 4) for IgG4, DASGVTFTWTPSSGK (SEQ ID NO: 5) for IgA1, DASGATFTWTPSSGK (SEQ ID NO: 6) for IgA2, VSVFVPPR (SEQ ID NO: 7) for IgM, or DFTPPTVK (SEQ ID NO: 8) for IgE. For the monkey antibody, the amino acid sequence of the unique surrogate peptide for identifying antibody isotype is GPSVFPLAPSSR (SEQ ID NO: 9) for IgG1, GPSVFPLASCSR (SEQ ID NO: 10) for IgG2, GPSVFPLVSCSR (SEQ ID NO: 11) for IgG3, GPSVFPLASSSR (SEQ ID NO: 12) for IgG4, QIEVSWLR (SEQ ID NO: 13) for IgM, or DPSGATFTWTPSSGK (SEQ ID NO: 14) for IgA.

Example 2. Develop a LC-MRM-MS Method to Identify and Quantify the ADA Isotypes

A MRM (multiple reaction monitoring) method based on LC-MS, for example, a LC-MRM-MS method, for isotyping and quantification of ADAs is developed, including selecting unique surrogate peptides for each isotype or subclass of monkey or human antibodies, developing a MRM method on the triple quadrupole mass spectrometer, and determining instrument detection limit.

LC-MRM-MS methods were successfully developed to identify and quantify the isotypes of human or monkey ADAs. After the peptide screening with LC-MS, quantifying and confirming peptides were selected for MRM quantitation. A quantifying peptide was chosen for quantification of each intact ADA. Another peptide from a different location of the same ADA, e.g., confirmation peptide, was chosen to confirm the data accuracy of the quantifying peptide and the integrity of the protein primary structure in the samples. The derived data based on the quantifying peptide were reported for the quantification of the ADA isotype. The derived data based on confirming peptide were used to evaluate the data agreement between quantifying and confirming peptides. The MRM ion transition for each peptide was determined on the basis of the product ion spectra in which the most prominent product ion was selected. The MS parameters (gas flow-rate, temperature, electrospray voltage, declustering potential, collision energy, and collision cell exit-potential) were optimized by analyzing the tryptic peptides with varied values for each MS parameter. (Jiang et al., Innovative Use of LC-MS/MS for Simultaneous Quantitation of Neutralizing Antibody, Residual Drug, and Human Immunoglobulin G in Immunogenicity Assay Development, Analytic Chemistry, 2014, 86, page 2673-2680)

One quantifying peptide and one to two confirming peptides for each antibody isotype/subclass were identified. Forty transitions for the human ADAs and thirty transitions for the monkey ADAs were selected. Tables 3, 4 and 5 show the optimization of a LC-MRM-MS method for monkey ADA isotyping, including amino acid sequences of the unique surrogate peptides and confirming peptides for each antibody isotype, precursor ion, product ion, collision energy, and monitoring over time.

TABLE 3

List of unique peptides for isotyping monkey ADA to optimize LC-MRM-MS methods.

| Isotype | Unique Peptide (monkey) | Precursor ion | Product ion | Collision Energy |
|---|---|---|---|---|
| IgG1 | GPSVFPLAPSSR (SEQ ID NO: 9) | 607.83 | 874.4781 727.4097 | 16.8 |
| IgG2 | GPSVFPLASCSR (SEQ ID NO: 10) | 639.319 | 937.4560 790.3876 | 23.8 |
| IgG3 | GPSVFPLVSCSR (SEQ ID NO: 11) | 653.3346 | 965.4873 818.4189 | 27.3 |
| IgG4 | GPSVFPLASSSR (SEQ ID NO: 12) | 602.8197 | 864.4574 717.3890 | 22.7 |
| IgM | QIEVSWLR (SEQ ID NO: 13) | 515.7876 | 789.4254 561.3144 | 17.0 |
| IgA | DPSGATFTWTPSSGK (SEQ ID NO: 14) | 769.8597 | 863.4258 475.2511 | 30.9 |

TABLE 4

List of confirming peptides for isotyping monkey ADA to optimize LC-MRM-MS methods.

| Isotype | Confirming Peptide (monkey) | Precursor ion | Product ion | Collision Energy |
|---|---|---|---|---|
| IgG1 | ALPAPIQK (SEQ ID NO: 15) | 419.2633 | 653.3981 485.3082 | 17.0 |
| IgG | STSESTAALGCLVK (SEQ ID NO: 16) | 475.2414 | 689.4015 576.3174 | 12.3 |
|  | VVSVLTVTHQDWLNGK (SEQ ID NO: 17) | 599.3282 | 617.3406 318.1772 | 25.8 |
|  | GLPAPIEK (SEQ ID NO: 2) | 412.7475 | 654.3821 486.2922 | 13.8 |
| IgM | DWLSQSVFTCR (SEQ ID NO: 18) | 699.8272 | 984.4567 583.2657 | 25.7 |
|  | CTVTHTDLPSPLK (SEQ ID NO: 19) | 490.2537 | 541.3344 147.1128 | 15.8 |
| IgA | GFSPEDVLVR (SEQ ID NO: 20) | 559.7957 | 827.4621 414.2347 | 12.4 |

TABLE 5

Multiple reaction monitoring at different time points for monkey ADA isotyping.

| | Time (min) | % A | % B | Flow (mL/min) | Gradient |
|---|---|---|---|---|---|
| Gradient | 0 | 95 | 5 | 0.4 | |
| | 2 | 95 | 5 | 0.4 | |
| | 10 | 75 | 25 | 0.4 | |
| | 11 | 10 | 90 | 0.4 | |
| | 12 | 10 | 90 | 0.4 | |
| | 13 | 95 | 5 | 0.4 | |
| | 15 | 95 | 5 | 0.4 | |

Tables 6 and 7 show the optimization of a LC-MRM-MS method for human ADA isotyping, including amino acid sequences of the unique surrogate peptides for each antibody isotype, precursor ion, product ion, collision energy, and monitoring over time.

TABLE 6

List of unique peptides for isotyping human ADA to optimize LC-MRM-MS methods.

| Isotype | Unique Peptide (human) | Precursor ion | Product ion | Collision Energy |
|---|---|---|---|---|
| IgG1 | GPSVFPLAPSSK (SEQ ID NO: 1) | 593.8270 | 699.4036 | 22.4 |
| IgG2 | GLPAPIEK (SEQ ID NO: 2) | 412.7475 | 654.3821 | 13.8 |
| IgG3 | WYVDGVEVHNAK (SEQ ID NO: 3) | 472.9017 | 697.3628 | 18.2 |
| IgG4 | GLPSSIEK (SEQ ID NO: 4) | 415.7345 | 660.3563 | 13.9 |
| IgA1 | DASGVTFTWTPSSGK (SEQ ID NO: 5) | 770.8675 | 475.2511 | 27.9 |
| IgA2 | DASGATFTWTPSSGK (SEQ ID NO: 6) | 756.8519 | 863.4258 | 21.5 |
| IgM | VSVFVPPR (SEQ ID NO: 7) | 450.7687 | 615.3613 | 15.0 |
| IgE | DFTPPTVK (SEQ ID NO: 8) | 452.7424 | 541.3344 | 15.0 |

TABLE 7

Multiple reaction monitoring at different time points for human ADA isotyping.

| | Time (min) | % A | % B | Flow (mL/min) | Gradient |
|---|---|---|---|---|---|
| Gradient | 0 | 95 | 5 | 0.4 | |
| | 2 | 95 | 5 | 0.4 | |
| | 10 | 75 | 25 | 0.4 | |
| | 11 | 10 | 90 | 0.4 | |
| | 12 | 10 | 90 | 0.4 | |
| | 13 | 95 | 5 | 0.4 | |
| | 15 | 95 | 5 | 0.4 | |

Example 3. Determine Instrument Detection Limit

Figure 3:
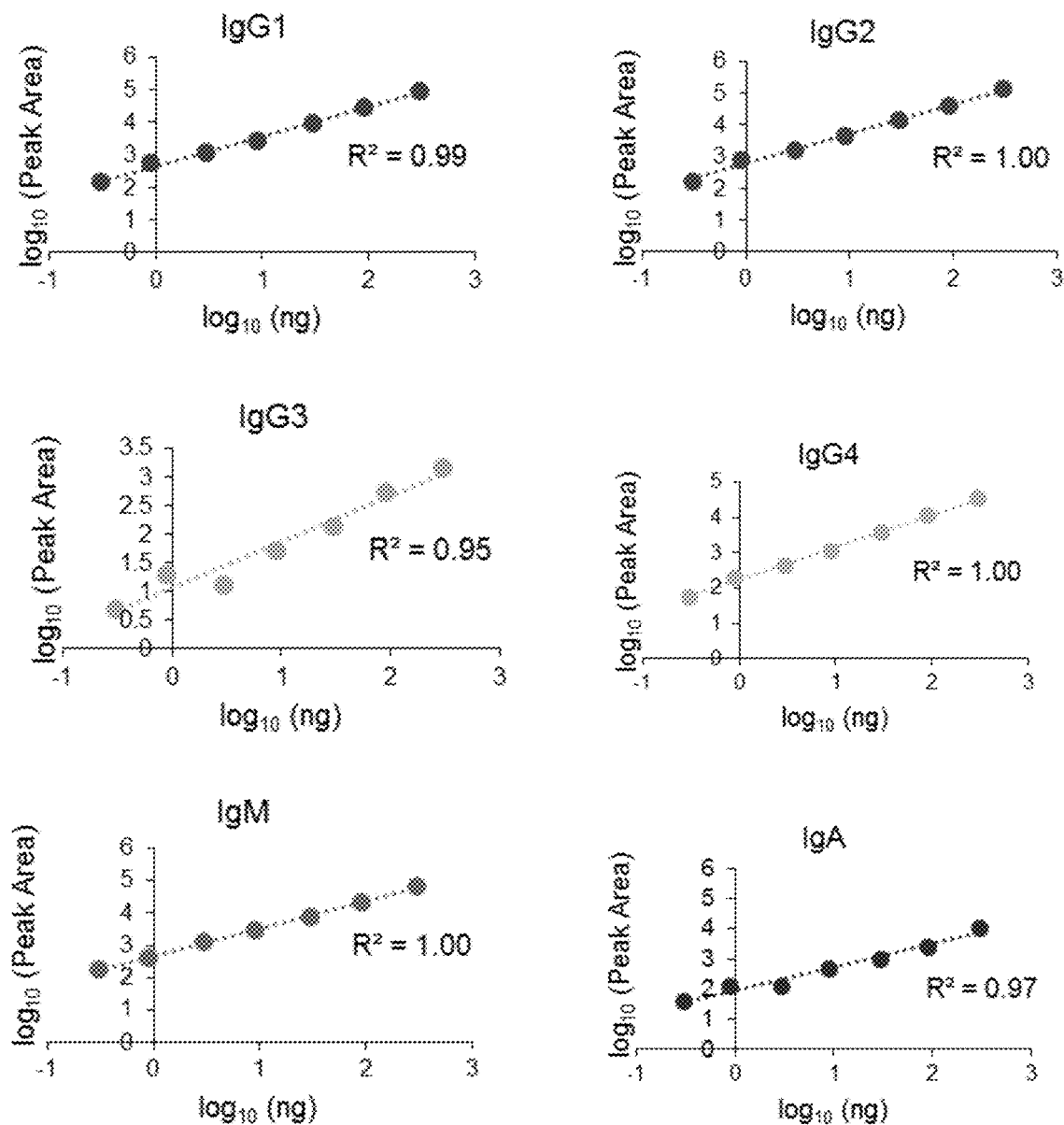
FIG. 3 shows the determination of instrument detection limit using a triple quadrupole LC-MS according to an exemplary embodiment. Different amounts of peptides of immunoglobulins were tested including 0.3 ng, 0.9 ng, 3 ng, 9 ng, 30 ng, 90 ng, and 300 ng. Monkey IgG1, IgG2, IgG3, IgG4, IgM, and IgA were tested according to an exemplary embodiment.

The instrument detection limit was determined using a triple quadrupole LC-MS, such as 6495C Triple Quadrupole LC/MS from Agilent Technologies. Monkey IgG, IgM, or IgA were diluted in BSA (bovine serum albumin) matrix. Different amounts of peptides of immunoglobulins were tested, including 0.3 ng, 0.9 ng, 3 ng, 9 ng, 30 ng, 90 ng, and 300 ng. FIG. 3 shows the testing results for monkey IgG1, IgG2, IgG3, IgG4, IgM, and IgA regarding linearity and instrument detection limit. The LC method can be optimized within 15 minutes. The results of the confirming peptides had good agreement with their corresponding surrogate peptides, suggesting accurate quantitation with the LC-MRM-MS methods and good integrity of the protein primary structures during sample storage and treatments. The developed LC-MRM-MS methods are able to detect as low as 0.3 ng of quantitated peptides from each ADA isotype on a triple quadrupole LC-MS, such as 6495C Triple Quadrupole LC/MS from Agilent Technologies.

Example 4. Immunocapture of ADAs Using Antibody Drugs

Two types of immunocapture methods for isolating ADAs from serum samples were developed using antibody drugs, wherein the ADAs can specifically bind to the antibody drugs. In the first method, the antibody drugs were biotinylated. The biotinylated antibody drugs which were bound to streptavidin coated magnetic beads were used to capture ADAs in human or monkey serum samples. In the second method, antibody drugs were cross-linked directly to the magnetic beads using primary amine-epoxy reaction through a lysine residue of the drug.

The drug-beads, for example, biotinylated drug-beads or cross-linked drug-beads, were used to capture ADAs from human or monkey serum samples by conducting an incubation step, wherein the drug-beads were incubated with serum sample containing ADAs in an incubation buffer to capture the ADAs. The magnetic beads were subsequently isolated using a magnet. The isolated beads were subsequently washed with a washing solution. Thereafter, the isolated beads were subjected to an elution solution to isolate ADAs from the drug-beads.

ADA-Std, a monkey IgG1 monoclonal anti-human kappa light chain antibody, was used as ADA positive control to optimize the immunocapture of ADAs. ADA-Std was diluted in monkey serum to mimic serum samples containing ADAs. However, for developing a MS method targeting ADAs captured from monkey serum samples, mouse serum was used to dilute ADA-Std to reduce the nonspecific interactions.

Figure 4:
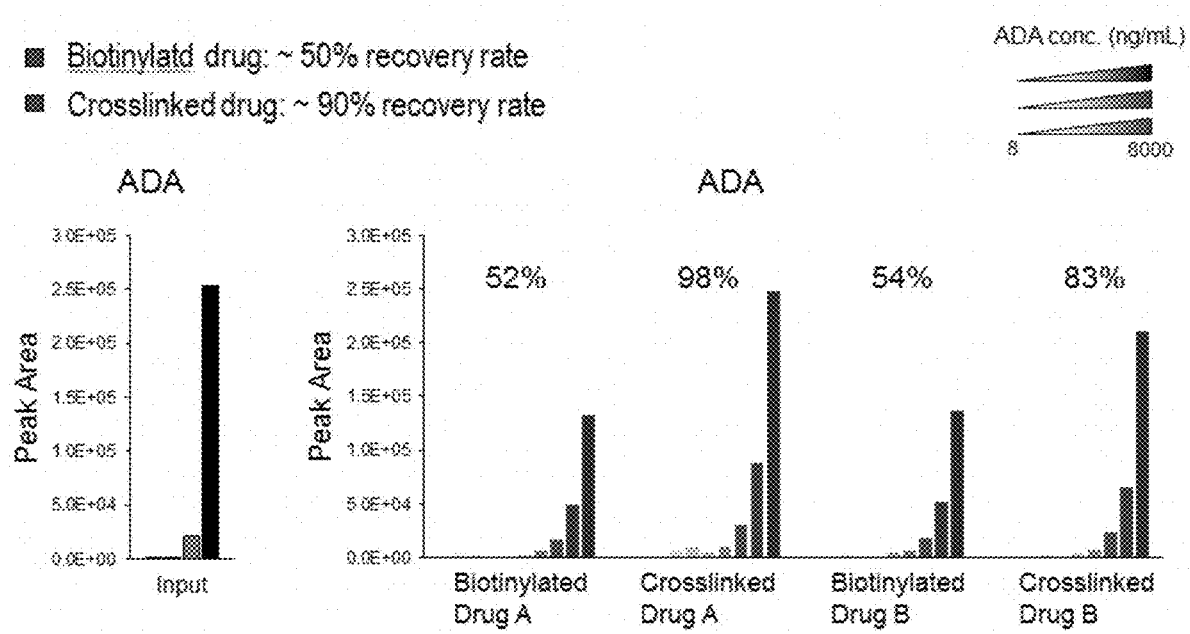
FIG. 4 shows the recovery rates of ADAs using biotinylated drug-beads or cross-linked drug beads according to an exemplary embodiment.

The recovery rates of ADAs using biotinylated drug-beads and cross-linked drug beads were compared. It is unexpected that the use of cross-linked drug beads to capture ADAs from serum samples has high recovery rates of about 83-98%. To the contrary, the use of biotinylated drug-beads to capture ADAs from serum samples can only achieve about 52-54% recovery rates. In these experiments, ADA-Std, shown as input in FIG. 4, was used as positive control for the comparisons. As shown in FIG. 4, when cross-linked drug A-beads were used, the recovery rate of ADAs was 98%. When cross-linked drug B-beads were used, the recovery rate of ADAs was 83%. However, when biotinylated drug A-beads were used, the recovery rate of ADAs was 52%. When biotinylated drug B-beads were used, the recovery rate of ADAs was 54%. Therefore, it is an unexpected advantage that the use of cross-linked drug-beads to capture ADAs from serum sample can achieve high recovery rates of ADAs.

Example 5. Optimizing the Enzymatic Digestion Method

The enzymatic digestion methods were optimized to improve the linearity and consistency of ADA identification and quantification. The ADAs which were isolated from the serum samples by the immunocapture method were subjected to drying, such as SpeedVac drying. The dried ADAs were dissolved in a suspension solution and subsequently subjected to enzymatic digestions, such as trypsin digestion, for quantification using LC-MS. Various suspension solutions were used to optimize the enzymatic digestion method, including the use of a denaturation solution, such as 8 M urea solution.

Figure 5A:
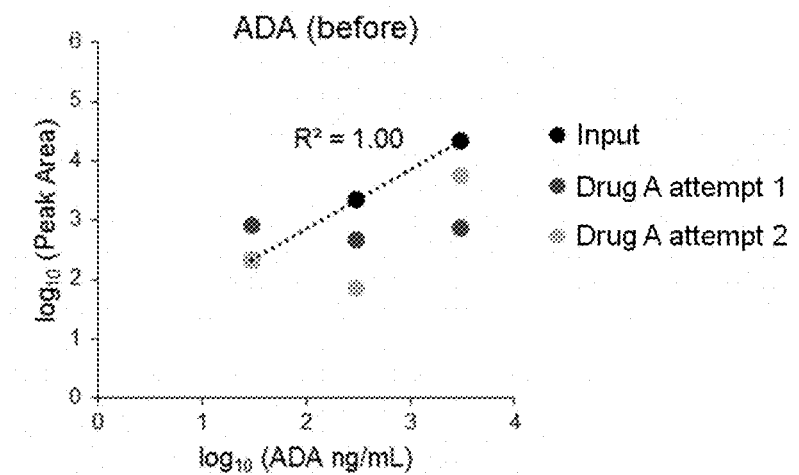
FIGS. 5A and 5B show the use of drug A or drug B to capture ADAs in the presence of a denaturation solution to dissolve the dried ADAs prior to subjecting to the enzymatic digestion according to an exemplary embodiment.
Figure 5B:
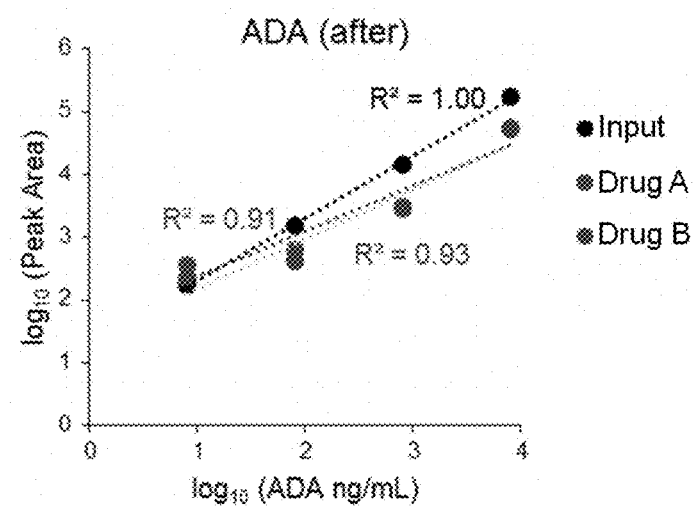

It is an unexpected advantage that the use of a denaturation solution to suspend the isolated ADAs for the enzymatic digestion can significantly improve the consistency and linearity of ADA identification and quantification as shown in FIG. 5. Purified ADA-Std was used as the positive control for these experiments. Dried ADA-Std was dissolved in the suspension solution directly prior to subjecting to the enzymatic digestion without going through the steps of immunocapture. ADA-Std was shown as input in FIG. 5. FIG. 5A shows the use of drug A to capture ADAs without using a denaturation solution for dissolving the dried ADAs. FIG. 5B shows the use of drug A or drug B to capture ADAs in the presence of a denaturation solution for dissolving the dried ADAs. As shown in FIG. 5B, when drug A or drug B was used to capture ADAs, the quantification of ADA capturing showed significantly improved consistency and linearity in the presence of a denaturation solution for dissolving the dried ADAs prior to subjecting to the enzymatic digestion. As shown in FIG. 5A, the consistency and linearity were not observed, when the denaturation solution was not used.

Example 6. Observation of Nonspecific Interactions

In order to improve the sensitivity and linearity of the immunocapture of ADAs for isotyping and quantification using LC-MS, experiments were designed to observe the nonspecific interactions in serum. ADA-Std, for example, a monkey IgG1 monoclonal anti-human kappa light chain antibody, was used as an ADA positive control, to develop and optimize the immunocapture and LC-MS assays for ADA isotyping and quantification. ADA-Std was diluted in mouse or monkey serum for the testing ranges of from 1.5 ng/ml to 10 µg/ml with three-fold dilution. ADA-Std was diluted in monkey serum to mimic serum samples containing ADAs. ADA-Std was subjected to enzymatic digestions and LC-MS assays without going through the steps of immunocapture.

Figure 6:
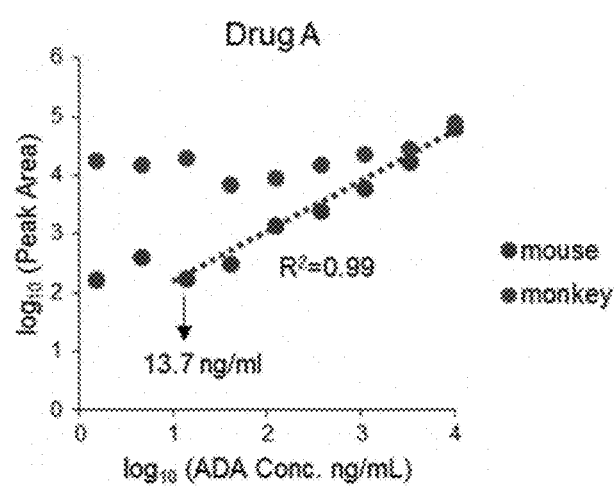
FIG. 6 shows nonspecific interaction in the presence of monkey serum according to an exemplary embodiment.
Figure 6:
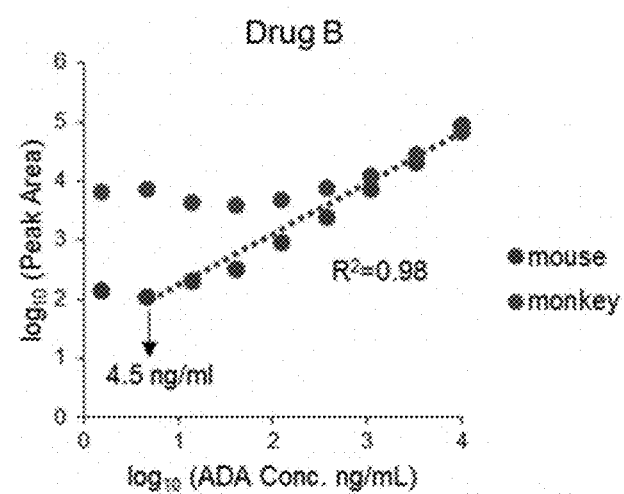

Drug A or drug B was used in the immunocapture method to isolate ADAs from monkey serum samples. The isolated ADAs were diluted in mouse or monkey serum and subsequently subjected to enzymatic digestions and LC-MS assays. As shown in FIG. 6, the addition of monkey serum can cause nonspecific interactions and high background noise which can lead to the reduction of consistency and linearity of the quantification. The testing results show good linearity in mouse serum.

ADA-Std was diluted in monkey serum to mimic serum samples containing ADAs. The detection of IgG1 signals can be a combination of the ADA-Std signal and endogenous IgG1 from monkey serum. In contrast, any other antibody isotypes detected can be endogenous antibodies resulted from nonspecific binding from monkey serum.

Example 7. Optimizing the Incubation Condition for Immunocapture

Since certain components in monkey serum can cause nonspecific interactions which lead to high background noises, the immnocapture method was further optimized to increase the sensitivity and consistency for the isotyping and quantification of ADAs using LC-MS assays. The drug which was used to capture ADAs was incubated with monkey serum sample containing ADAs in various incubation conditions including the incubation at room temperature for 1 hour or at 4 degree C. overnight. It was surprising to discover that the incubation condition at room temperature for 1 hour provided significant reduction in background noises. The background noises were low with improved consistency and linearity when the incubation was conducted at room temperature for 1 hour, therefore it enhanced the signals of ADAs in LC-MS assays.

Figure 7A:
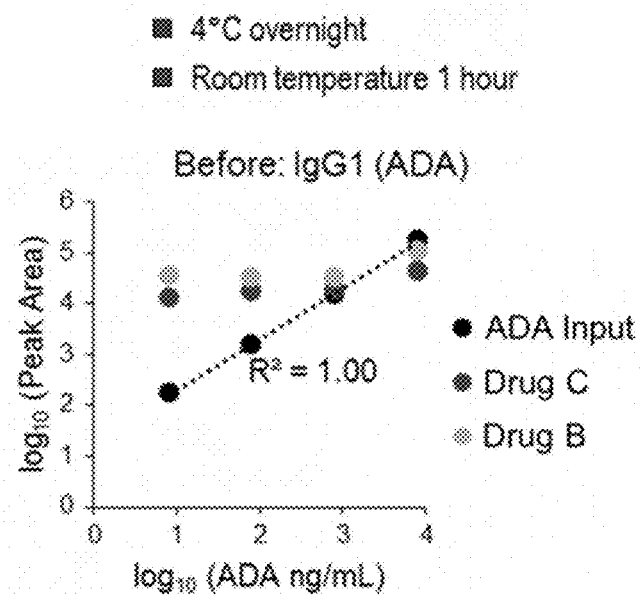
FIG. 7 shows optimization of incubation conditions for immnuocapture including incubation conditions including the incubation at room temperature for 1 hour or at 4 degree C. overnight according to an exemplary embodiment.
Figure 7B:
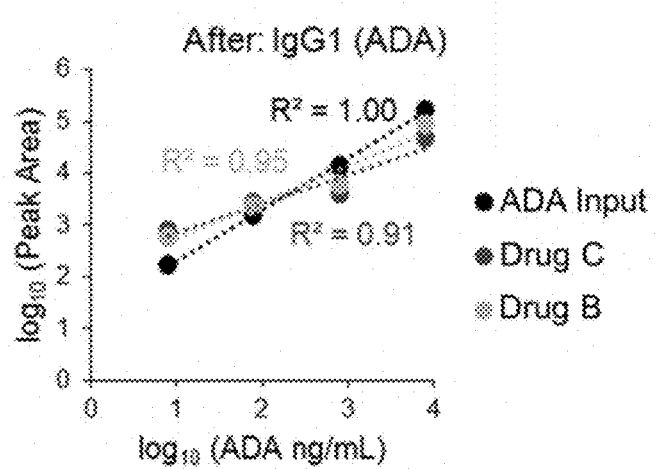
Figure 8:
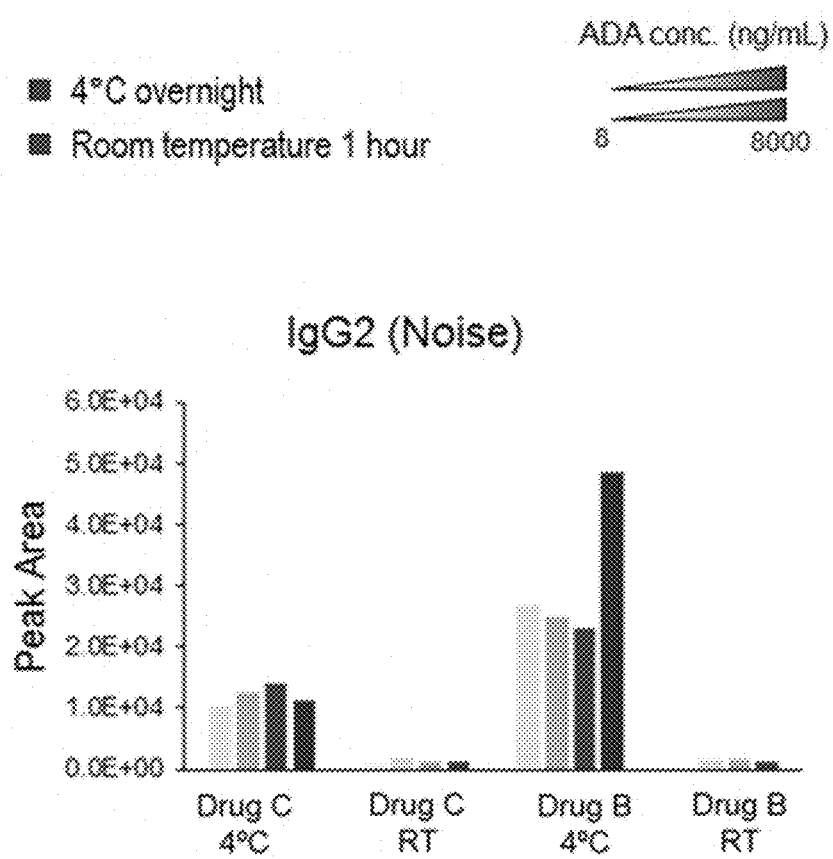
FIG. 8 shows optimization of incubation conditions for immnuocapture using IgG2 as a noise indicator according to an exemplary embodiment.

As shown in FIG. 7A, when drug B or drug C was incubated with the monkey serum samples at 4 degree C. overnight, the quantitation of ADA-IgG1 lacked linearity and consistency. As shown in FIG. 7B, when drug B or drug C was incubated with the monkey serum samples at room temperature for 1 hour, the quantitation of ADA-IgG1 showed excellent linearity and consistency. ADA-Std was used as positive control in these experiments and was indicated as ADA input in FIG. 7. FIG. 8 shows the optimization of incubation conditions for immnuocapture using IgG2 as a noise indicator. As shown in FIG. 8, drug B or drug C was used to capture ADAs from monkey serum samples, the incubation condition at room temperature for 1 hour provided less noises for isotyping and quantifying IgG2 in comparing to the incubation condition at 4 degree C. overnight.

Example 8. Optimizing Immunocapture by Interrupting Interactions in Serum

There are various specific or nonspecific interactions among components in serum, such as the binding between antigens and antibodies, or aggregations among proteins. In order to reduce high background noises, the immunocapture method was further optimized to reduce the nonspecific or specific interactions in serum. It was unexpected to discover that the addition of acidic solutions to serum samples prior to performing immunocapture can significantly reduce the background noises for identification and isotyping the isolated ADAs using LC-MC assays.

In general, the pH range of the serum sample is about pH 8.0. An acidic solution, such as 300 mM acetic acid, was added to the serum sample to reach an acidic pH range for performing acid dissociations among the components in serum, such as about pH 3.6. The pH of the acidic serum sample was subsequently adjusted to about pH 4.5 for performing immunocapture using drug-beads, such as the pH adjustment of adding HBST buffer, for example, 10 mM HEPES (4-(2-hydroxyethyl)-1-piperazineethanesulfonic acid), 150 mM sodium chloride, 3 mM EDTA (ethylenediaminetetraacetic acid) and 0.2% Tween-20 (polysorbate 20) at pH 7.4.

The acid dissociation treatments of the serum samples provided unexpected advantages of significant reduction in background noises. Further optimization of acid dissociation was performed using two acidic conditions 1 and 2. The method of acidic condition 1 comprises adding 1 µl of 5 M acetic acid into 49 µL of monkey serum sample to reach final concentration of acetic acid at 300 mM, and incubating for 1 hour. The method of acidic condition 2 comprises adding 50 µl of 600 mM acetic acid into 50 µL of monkey serum sample to reach final concentration of acetic acid at 300 mM, and incubating for 1 hour.

Figure 9:
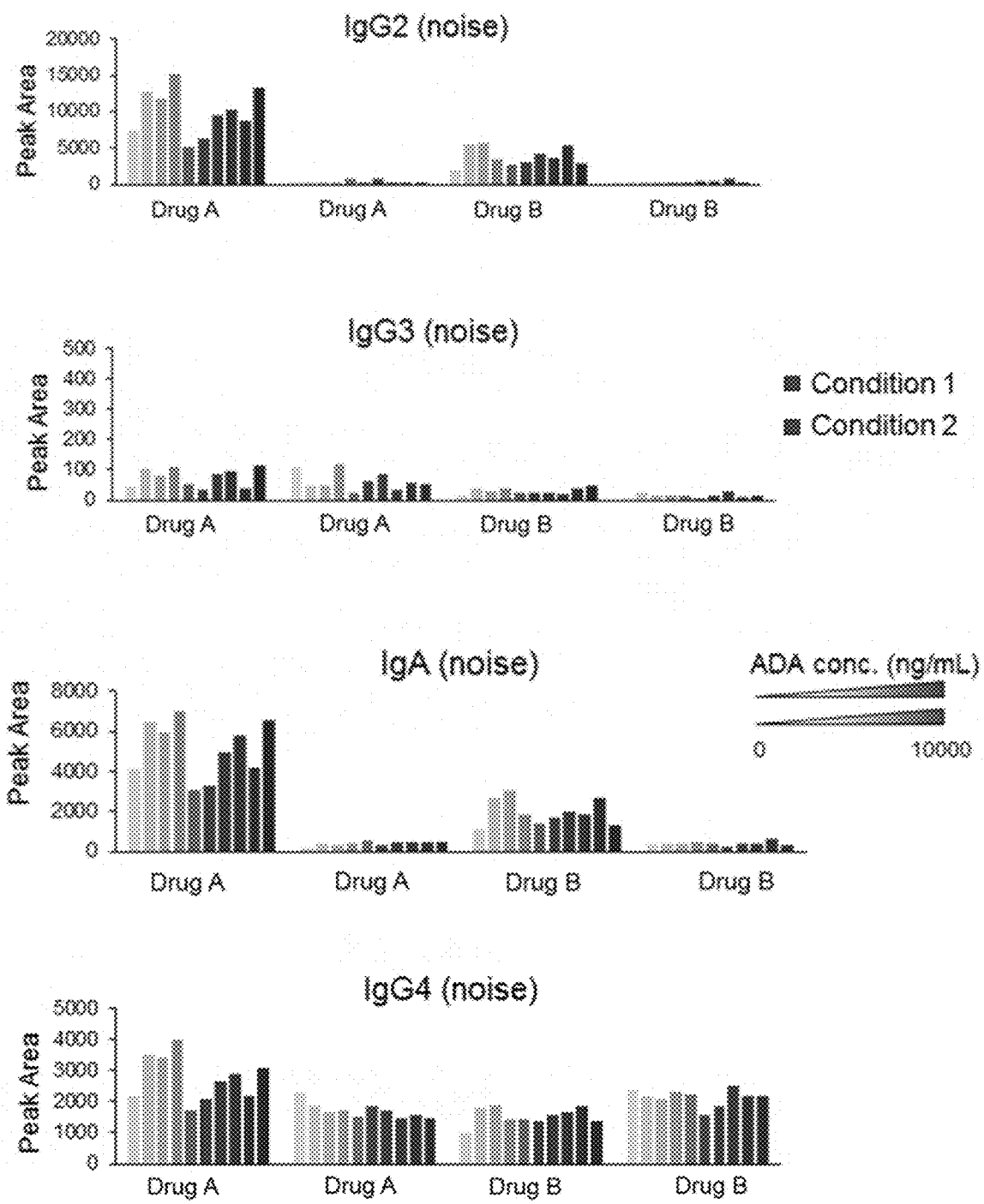
FIG. 9 shows optimization of immunocapture by interrupting interactions in serum using acidic conditions according to an exemplary embodiment. Condition 1: add 1 µL 5 M acetic acid into 49 µL monkey serum, incubate for 1 hour (final acetic acid concentration of 300 mM). Condition 2: add 50 µL 600 mM acetic acid into 50 µL monkey serum, incubate for 1 hour (final acetic acid concentration of 300 mM).

As shown in FIG. 9, drug A or drug B was used to capture ADAs. The acidic condition 2 provided significant reduction in background noise for the isotyping and quantification of the ADAs regarding IgG2, IgG3, and IgA in comparing to acidic condition 1. The acidic condition 2 is a preferable condition for performing acid dissociation for immunocapture of the IgG2, IgG3, and IgA isotypes of ADAs using drug A or B. However, both acidic conditions 1 and 2 did not provide significant reduction in background noises for the isotyping and quantification of IgG4. It indicated that further optimization was needed to reduce the high background noise for isotyping and identification of IgG4. It also indicates that the nonspecific interactions in serum are not significantly contributory to the high background noises for the isotyping and quantification of IgG4.

Example 9. Immunocapture Using Fab of IgG Drug 9.1. Isotyping and Quantification of IgG4 Isotype of ADAs.

Figure 10:
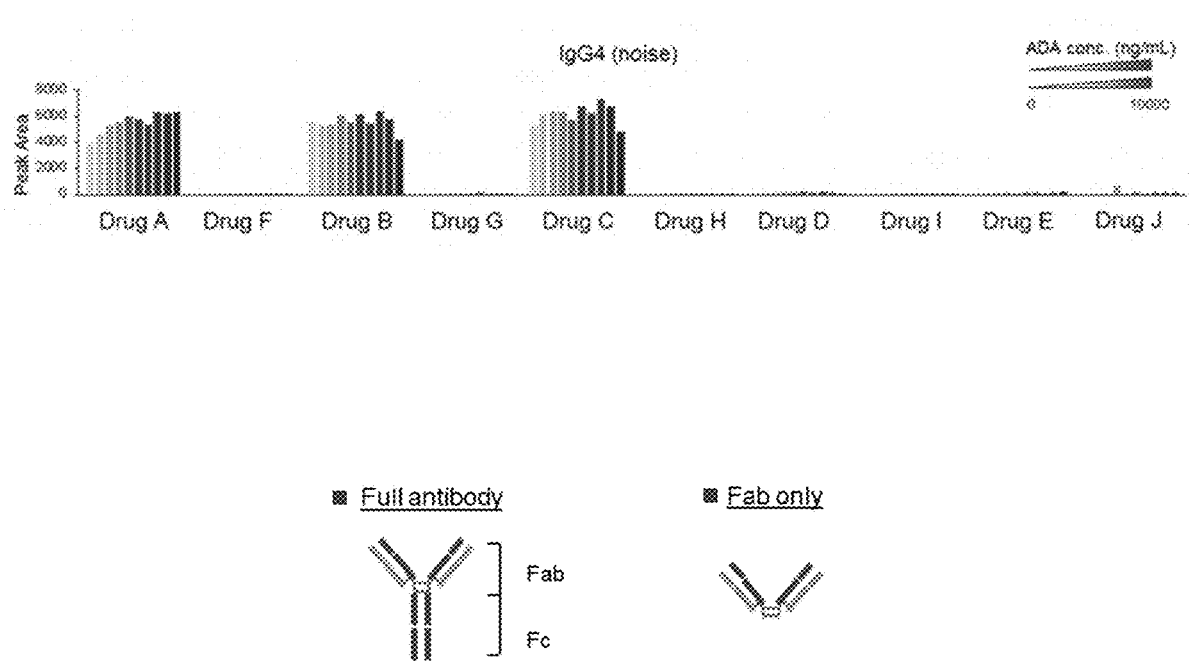
FIG. 10 shows use of Fab portions of IgG drugs to capture ADAs for the optimization of isotyping and quantification of ADA IgG4 according to an exemplary embodiment. Fab only drug eliminates serum IgG4 interactions to Fc region of IgG4 drugs. For IgG1, both full antibody and Fab only have low non-specific binding.

The antibody drug which comprised only Fab portion of IgG was used to capture ADAs to investigate the nonspecific interactions in serum to optimize the immunocapture method. As listed in Table 1, drugs A-E comprise the entire IgG molecules and drugs F-J comprise only Fab portions of the IgG molecules. As shown in FIG. 10, Fab only drug eliminates serum IgG4 interactions to Fc region of IgG4 drugs. For IgG1, both full antibody and Fab only have low non-specific binding. The use of Fab portions of IgG drugs to capture ADAs significantly reduced the background noises for isotyping and identification of IgG4 ADAs. In particular, when drug F, drug G and drug H were used for immunocapture of ADAs for the isotyping and quantification of IgG4 ADAs, the background noises were significantly reduced in comparing to the use of drug A, drug B, and drug C.

Drug A, drug B and drug C comprise the entire molecules of IgG4. Drug F, drug G and drug H comprise only the Fab portions of the IgG4. The test results indicate the endogenous IgG4 antibodies in monkey serum sample may play significant role for contributing to the high background noises. It is likely that the endogenous IgG4 antibodies in monkey serum sample may interact with the Fc regions of drug A, drug B and drug C, since these drugs include the whole molecules of IgG4. It is likely that the endogenous IgG4 antibodies in monkey serum sample may interact with the Fc regions of IgG4 drugs, such as the L445 residue in IgG4. Therefore, when drug F, drug G and drug H were used, the background noises were reduced or eliminated, since these drugs only contain the Fab regions of IgG4 and do not contain the Fc regions. It is likely that the endogenous IgG4 antibodies in monkey serum sample do not interact with the Fc regions of IgG1 drug according to the test results based on drug D and drug E.

9.2. Isotyping and Quantification of IgM Isotype of ADAs.

Figure 11:
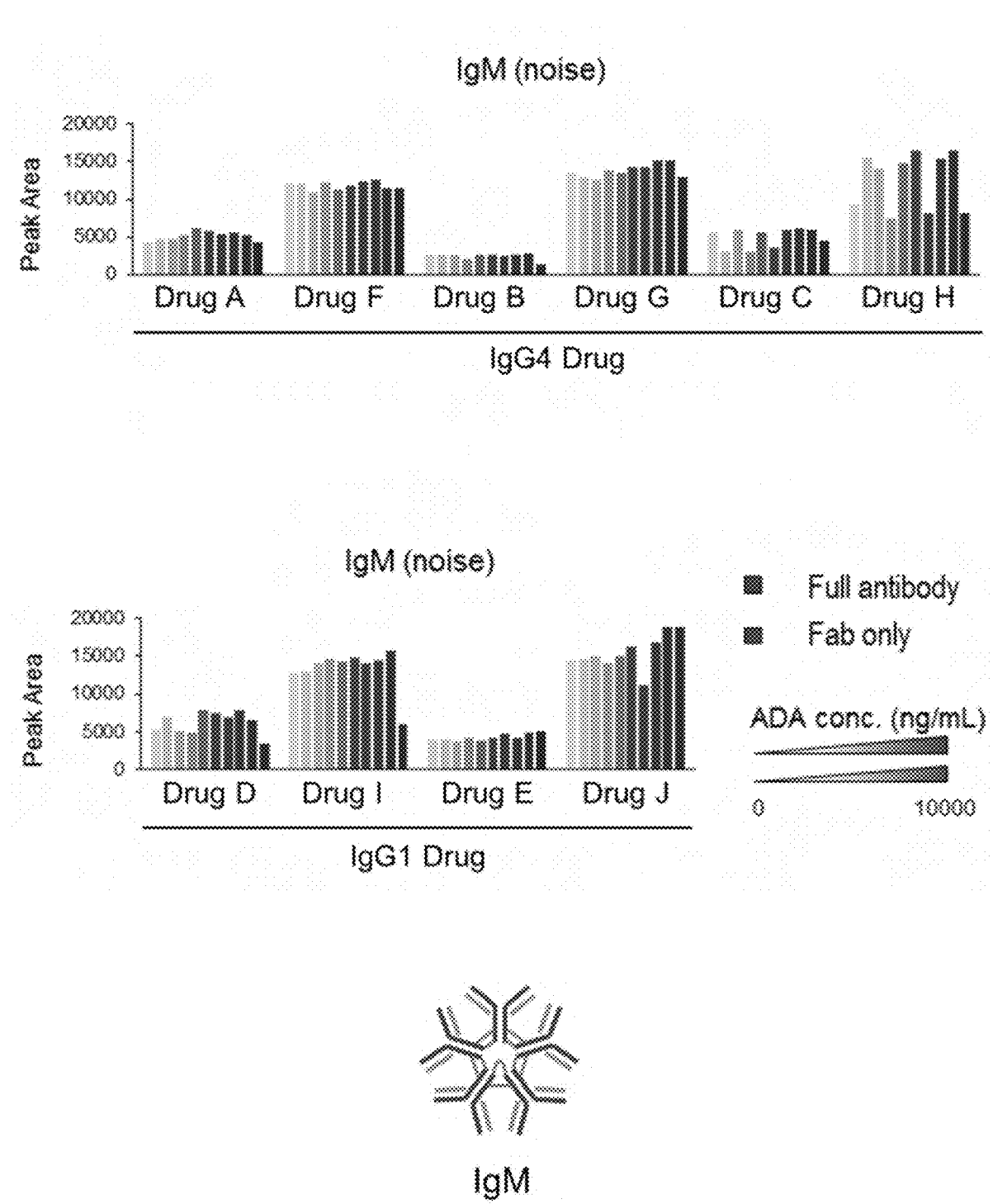
FIG. 11 shows use of Fab portions of IgG drugs to capture ADAs for isotyping and identification of IgM ADAs according to an exemplary embodiment. The results indicate that the interaction between serum IgM and drug Fab region causes high IgM background.

The antibody drugs which comprise only Fab portions of IgG molecule were used to capture ADAs to investigate the nonspecific interactions in serum to optimize the immunocapture method. As listed in Table 1, drugs A-E comprise the entire IgG molecules and drugs F-J comprise only Fab portions of the IgG molecules. As shown in FIG. 11, the use of Fab portions of IgG drugs to capture ADAs did not significantly reduced the background noises for isotyping and identification of IgM ADAs. The results indicate that the interaction between serum IgM and drug Fab region causes high IgM background. In particular, when drug F, drug G, drug H, drug I and drug J were used for immunocapture of ADAs for the isotyping and quantification of IgM, the background noises were high in comparing to the use of drug A, drug B, drug C, drug D and drug E.

Drug A, drug B, drug C, drug D and drug E comprise the entire molecules of IgG, e.g., IgG1 or IgG4. Drug F, drug G, drug H, drug I and drug J comprise only the Fab portions of the IgG molecules. The test results indicate that the endogenous IgM antibodies in monkey serum sample may play significant role for contributing to the high background noises by binding to the Fab portions of both IgG 1 drug and IgG4 drug. It indicated that further optimization was needed to reduce the high background noises for isotyping and identification of IgM.

Example 10. Determination of the Low Limit of Quantitation (LLOQ)

10.1. Preferred Immunocapture and Enzymatic Digestion Methods.

Figure 12:
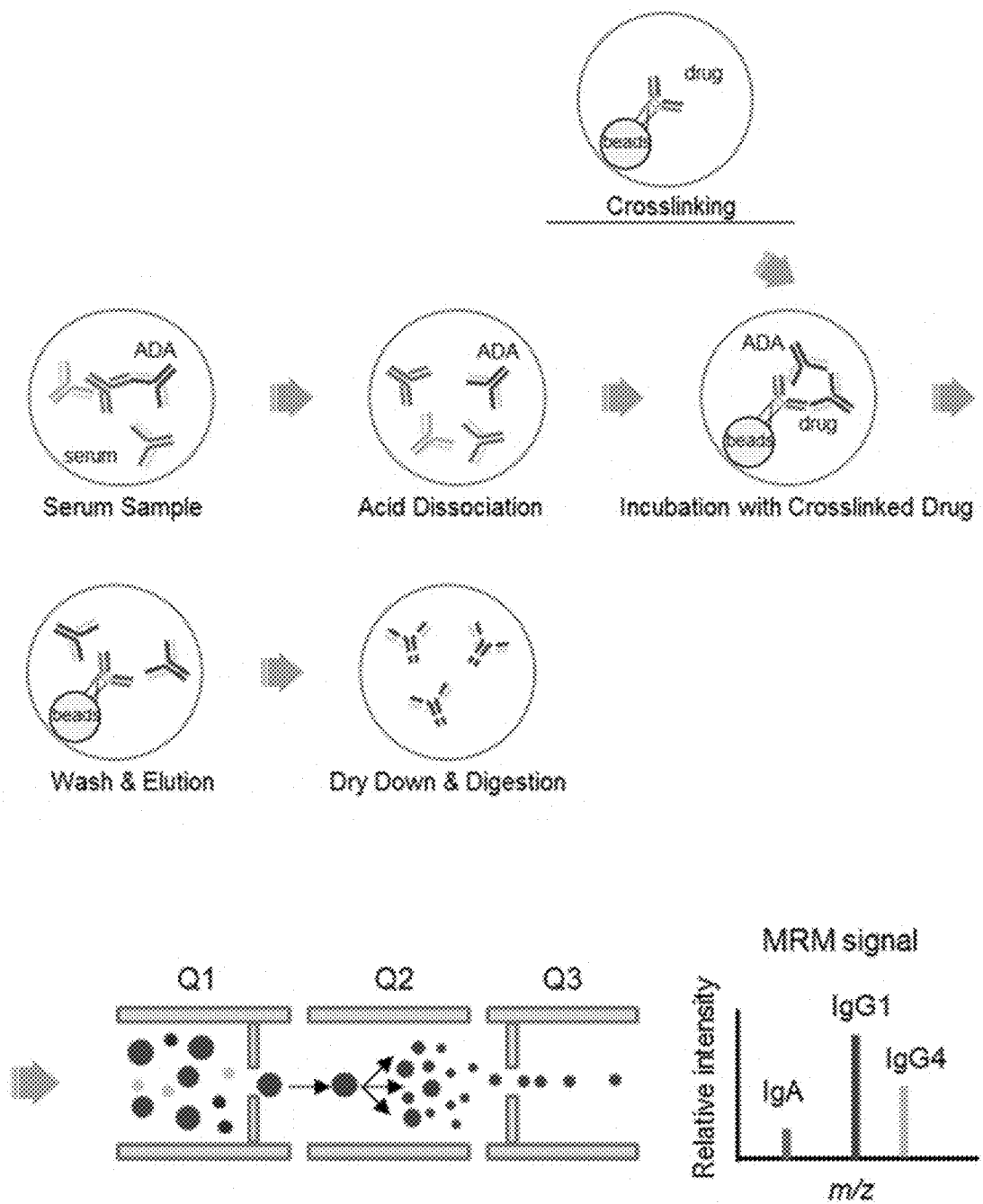
FIG. 12 shows preferred immunocapture, enzymatic digestion, and LC-MC methods for isotyping and quantification of ADAs according to an exemplary embodiment.

The low limit of quantitation (LLOQ) of peptide quantification in accordance with the concentration of ADAs was determined using the preferred immunocapture and enzymatic methods. The preferred immunocapture and enzymatic digestion methods which were used to generate calibration curves for the determination of LLOQ include treating a serum sample containing ADAs with an acidic solution for acid dissociation of the components in serum, subsequently incubating the serum sample with a drug which was cross-linked directly to beads for immunocapture of ADAs, isolating the beads, washing the isolated beads with a washing solution, subsequently isolating ADAs from the beads with an elution solution, and subjecting the isolated ADAs to an enzymatic digestion to generate a combination of peptides. The combination of peptides were subjected to LC-MS analysis for isotyping and quantification of ADAs. The preferred immunocapture and enzymatic methods are outlined in FIG. 12 as an example.

As an example, the acid dissociation was performed by adding 50 μL of 600 mM acetic acid to 50 μL of a serum sample and incubating for 1 hour at room temperature. Subsequently, the drug-beads were incubated with the serum samples at room temperature for 1 hour. As an example, 40 μL of 50 μg/mL of cross-linked drug was added to the serum sample which was diluted in 400 μL of 3% BSA (bovine serum albumin) in HBST buffer. Subsequently the beads were isolated. The isolated beads were washed with at least one washing solution at 0.5 mL, such as HBST buffer, and/or 3% BSA in HBST buffer. Subsequently the ADAs were isolated from the beads with an elution solution. As an example, 200 μL of elution solution, e.g., 0.1% formic acid/50% acetonitrile, was used to elude the ADAs from the beads. The isolated ADAs were dried down, such as using SpeedVac. The dried ADAs were suspended in denaturation solutions, such as 8 M urea. Subsequently, the isolated ADAs were subjected to enzymatic digestions, such as trypsin digestion, and LC-MS analysis for isotyping and quantification of ADAs.

10.2. Generation of Calibration Curve.

Figure 13:
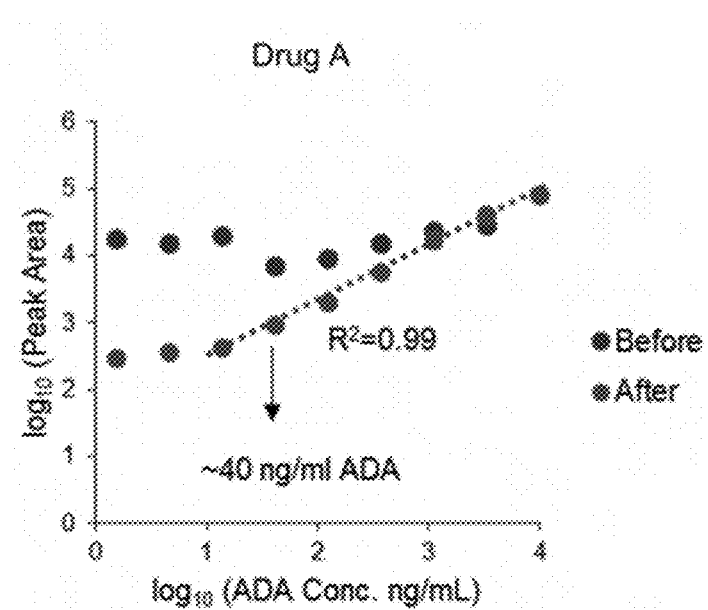
FIG. 13 shows the testing range of ADAs for generating calibration curves and determining limit of detection or limit of quantification using drug A or B before or after the method development for immunocapture according to an exemplary embodiment.
Figure 13:
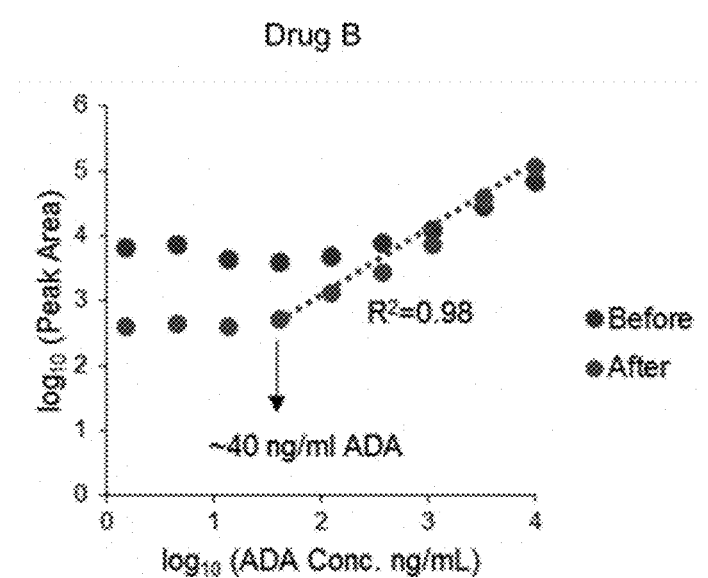

The calibration curves for detection and quantification of ADAs isotypes were generated using the ADA peptides which were obtained using the preferred immunocapture and enzymatic digestion methods as described above. The ADA-Std was used as a positive control which was diluted in monkey serum for the detection and quantification. As shown in FIG. 13, the testing range was from 1.5 ng/mL to 10 μg/mL of ADA with three fold dilution. Drug A or drug B was used for immunocapture of ADAs. A sufficient chromatographic response (signal-to-noise ratio) was observed in the LLOQ sample, and no interference peak was shown at the corresponding retention time. The limit of detection (LOD) was determined to be 40 ng/ml of ADA, when drug A or drug B was used for immunocapture of ADAs as shown in FIG. 13. The limit of quantification (LOQ) was determined to be 120 ng/ml of ADA, when drug A or drug B was used for immunocapture of ADAs as shown in FIG. 13. The LLOQ of 120 ng/mL of ADA was established for the isotyping and quantitation of ADAs using the immunocapture and LC-MS methods of the present application.

Example 11. Determination of Drug Tolerance Limit

The presence of therapeutic drugs in nonclinical monkey serum samples may compete with immunocapture reagents for binding to ADAs, also known as drug interference. To assess the assay tolerance to Drug A and Drug B present in serum samples, pooled monkey serum samples containing 500 ng/mL of ADA-PC were tested in the presence of different concentrations of Drug A or Drug B (ranging from 0.38 ng/mL to 10 μg/mL) to determine what concentrations of drug impacts both ADA quantitation and ADA detection.

Figure 14:
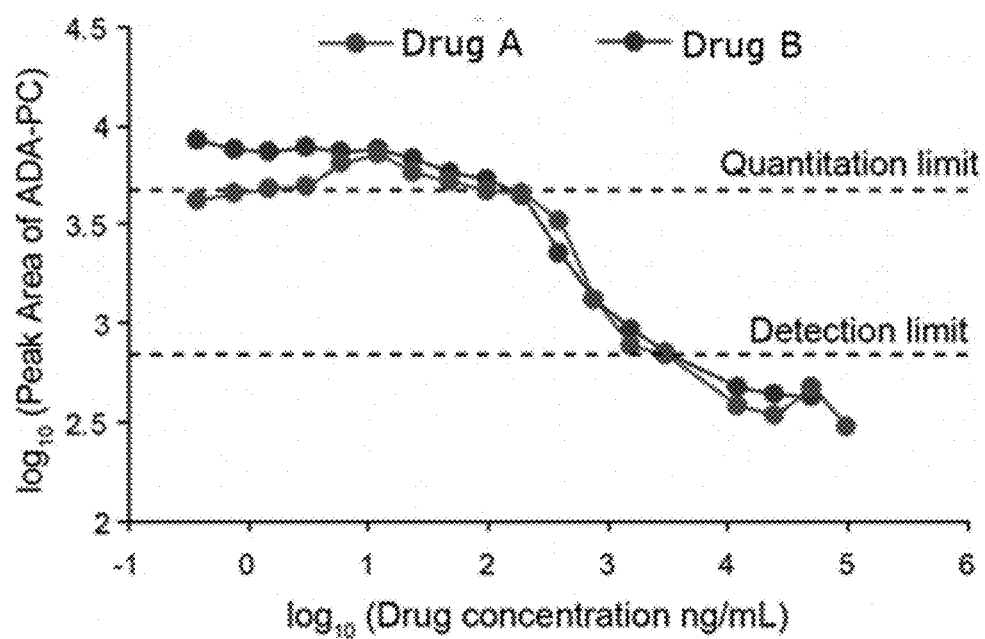
FIG. 14 shows the effect of varying concentrations of drug A or B on the quantitation and detection of ADAs according to an exemplary embodiment.

The quantitation of ADA-PC was not impacted by Drug A or Drug B until the drug concentration reached 195 ng/mL, as shown in FIG. 14. When the drug concentration was higher than 195 ng/mL, concentration of ADA-PC detected in the assay started to decrease, indicating the competing effect of drug in the sera for ADA binding.

Ligand binding ADA assays are non-quantitative and ADA concentrations in nonclinical studies are reported as either negative or positive with a titer (dilution) value which provides a relative quantitation of the antibody response. In the drug tolerance experiments, the ADA-PC can still be detected even at Drug A or Drug B concentration of 3.1 μg/mL, with ADA-PC signal 3-fold greater than assay background at this drug concentration.

Figure 15:
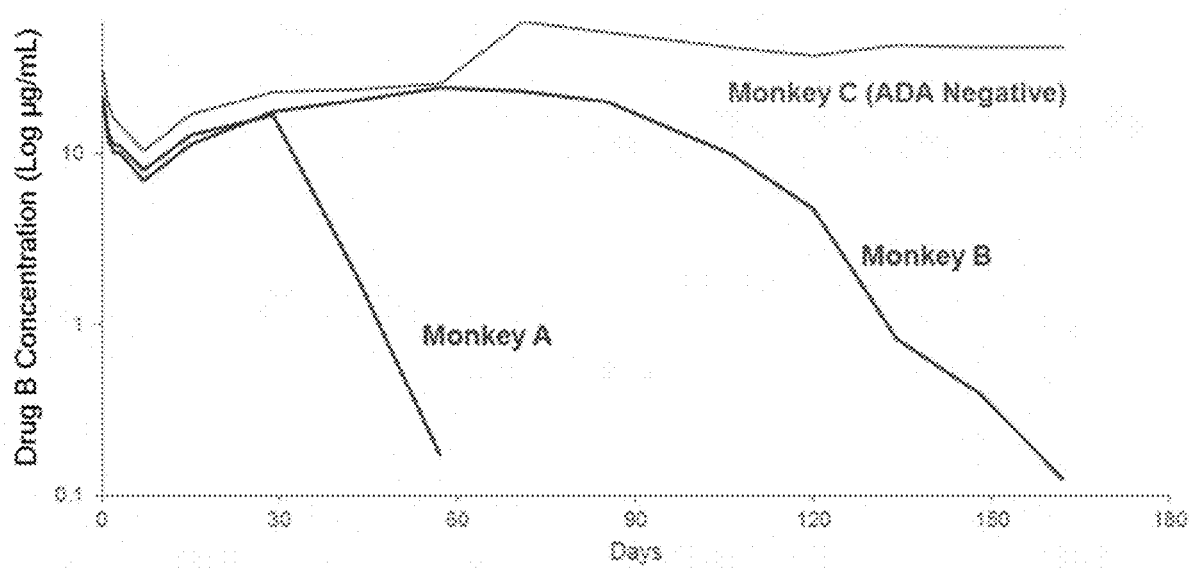
FIG. 15 shows the concentrations of drug B in the serum samples of monkey A or B over time in preclinical toxicology study according to an exemplary embodiment.

Example 12. Isotyping and Quantification of ADAs in Preclinical Toxicology Study in Monkeys The immunocapture and LC-MS methods of the present application were used for isotyping and quantification of ADAs in preclinical toxicology study in monkeys for drug B. Monkeys were treated with drug B at 1 mg/kg on weekly dose. The concentrations of drug B in the serum samples of the monkeys were monitored over time to access the toxicokinetics of monkeys A, B and C, as shown in FIG. 15. A summary of drug levels, mass spectrometry peak area of all ADA isotypes, converted ADA concentrations, and signal to noise ratio for monkey A and monkey B are shown in Table 8. The signal to noise ratio represents the ratio of peak area of a given sample to the pre-dose negative monkey serum sample. Monkey A had quick decays of the drug B concentrations within 60 days. The drug B concentrations in monkey B serum samples decayed gradually within 170 days. The concentrations of drug B in monkey C serum samples were stable without significant reduction over time.

TABLE 8

Summary of drug B levels, mass spectrometry peak area of all ADA isotypes, converted ADA concentrations, and signal to noise ratio.

| | | Days | | | | |
|---|---|---|---|---|---|---|
| | | 0 | 43 | 57 | 71 | 85 |
| Monkey A | Drug level (μg/mL) | BLQ | 1.94 | 0.174 | BLQ | BLQ |
| | Peak Area | 278 | 3309 | 10217 | 20911 | 28106 |
| | ADA conc. (μg/mL) | 0.03 | 0.34 | 1.06 | 2.17 | 2.92 |
| | Signal/Noise | 1.0 | 11.9 | 36.8 | 75.2 | 101.1 |

TABLE 8-continued

Summary of drug B levels, mass spectrometry peak area of all ADA isotypes, converted ADA concentrations, and signal to noise ratio.

| Monkey B | Drug level (μg/mL) | BLQ | 20.6 | 24.6 | 23.4 | 20.2 |
|---|---|---|---|---|---|---|
| | Peak Area | 829 | 1231 | 2002 | 1160 | 1521 |
| | ADA conc. (μg/mL) | 0.08 | 0.13 | 0.21 | 0.12 | 0.16 |
| | Signal/Noise | 1.0 | 1.5 | 2.4 | 1.4 | 1.8 |

| | | Days | | | | |
|---|---|---|---|---|---|---|
| | | 106 | 120 | 134 | 148 | 162 |
| Monkey A | Drug level (μg/mL) | BLQ | BLQ | BLQ | BLQ | BLQ |
| | Peak Area | 33451 | 39392 | 42783 | 54189 | 55203 |
| | ADA conc. (μg/mL) | 3.48 | 4.10 | 4.45 | 5.64 | 5.75 |
| | Signal/Noise | 120.3 | 141.7 | 153.9 | 194.9 | 198.6 |
| Monkey B | Drug level (μg/mL) | 10 | 4.79 | 0.828 | 0.396 | 0.124 |
| | Peak Area | 3425 | 3371 | 4443 | 5507 | 6986 |
| | ADA conc. (μg/mL) | 0.35 | 0.35 | 0.46 | 0.57 | 0.72 |
| | Signal/Noise | 4.1 | 4.1 | 5.4 | 6.6 | 8.4 |

Figure 16A:
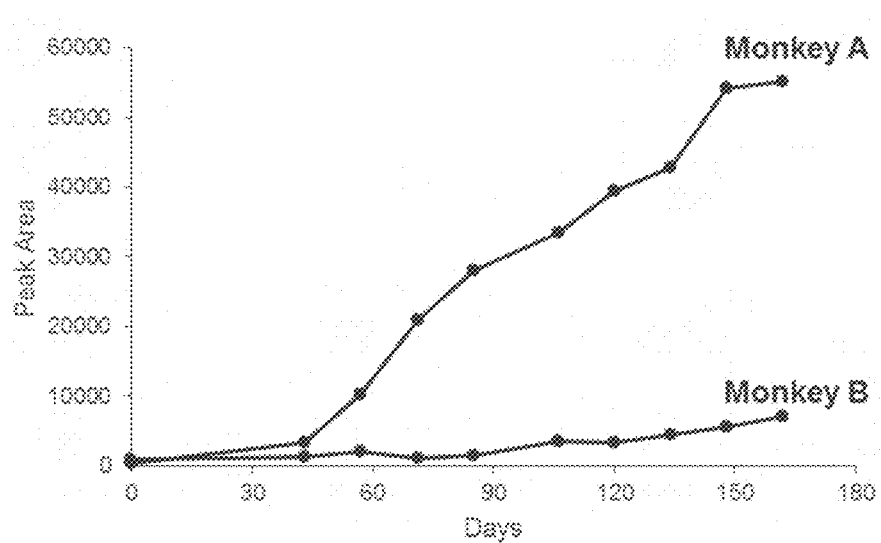
FIG. 16 shows the measurements of total quantities of ADAs in monkeys A and B according to an exemplary embodiment. The total quantities of ADAs in monkeys A and B were measured using the immunocapture-LC/MS methods of the present application as shown in FIG. 16A according to an exemplary embodiment. The total quantities of ADAs in monkeys A and B were measured using Ligand Binding Assay (LBA) as shown in FIG. 16B according to an exemplary embodiment.
Figure 16B:
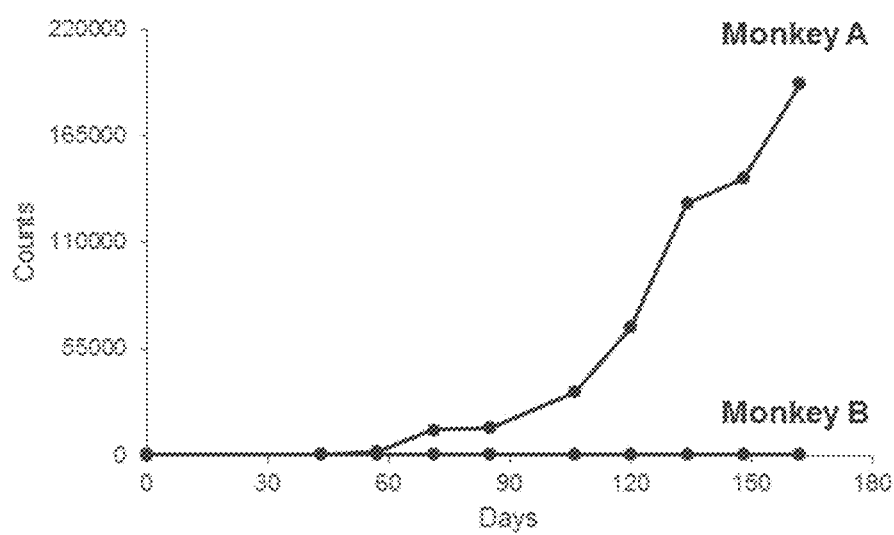

The serum samples of monkeys A, B and C were subjected to the isotyping and quantification of ADAs of drug B using the immunocapture and LC-MS methods of the present application. The test results of ADAs in monkey C were negative which indicated the non-existence of ADAs in monkey C. The total quantities of ADAs in monkeys A and B were measured using the immunocapture-LC/MS methods of the present application as shown in FIG. 16A. The total quantities of ADAs in monkeys A and B were measured using Ligand Binding Assay (LBA) as shown in FIG. 16B.

The test results of both immunocapture-LC/MS method and LBA were comparable showing similar trends of ADA quantities over time. The test results of both immunocapture-LC/MS methods and LBA for monkey A were comparable showing similar trends of increasing quantities of ADAs over time as shown in FIGS. 16A and 16B. These test results were consistent with the quick decays of the drug B concentrations within 60 days for monkey A as indicated in the toxicokinetics study of monkey A in FIG. 15. The measurements of total ADAs in monkey B using LBA were unable to detect the quantities of ADAs over time as shown in FIG. 16B. However, the measurements of total ADAs in monkey B using immunocapture-LC/MS methods were able to quantitate the gradual increases of ADAs concentrations within 170 days as shown in FIG. 16A, which were consistent with the toxicokinetics study of monkey B as showed in FIG. 15.

Figure 17A:
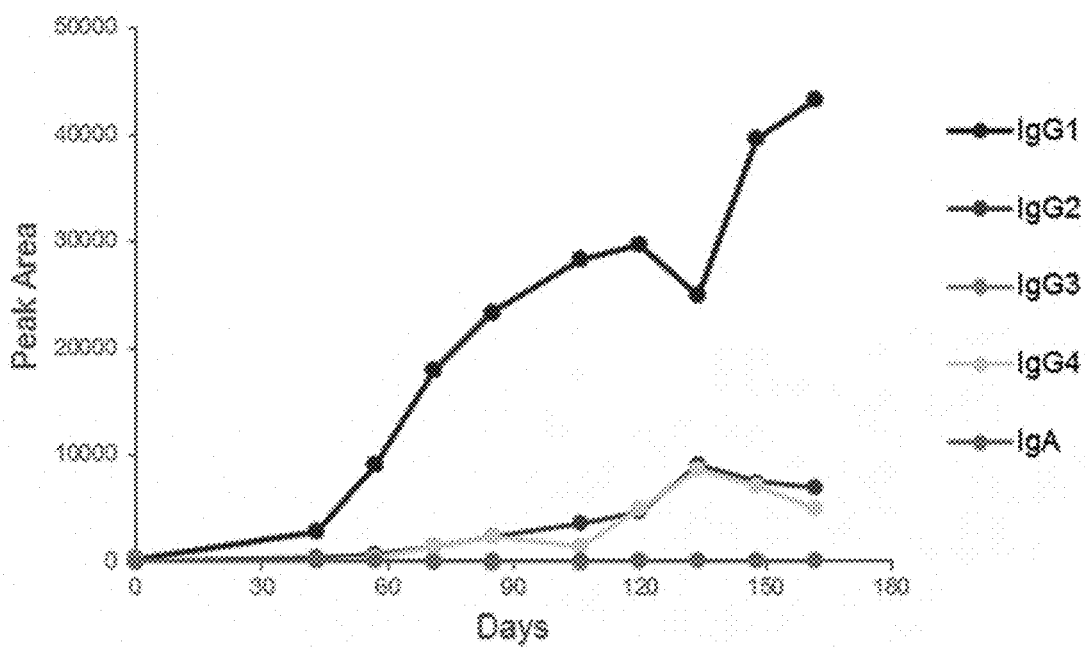
FIGS. 17A and 17B show the relative quantifications of ADA isotypes including the quantities of IgG1, IgG2, IgG3, IgG4 and IgA according to an exemplary embodiment.
Figure 17B:
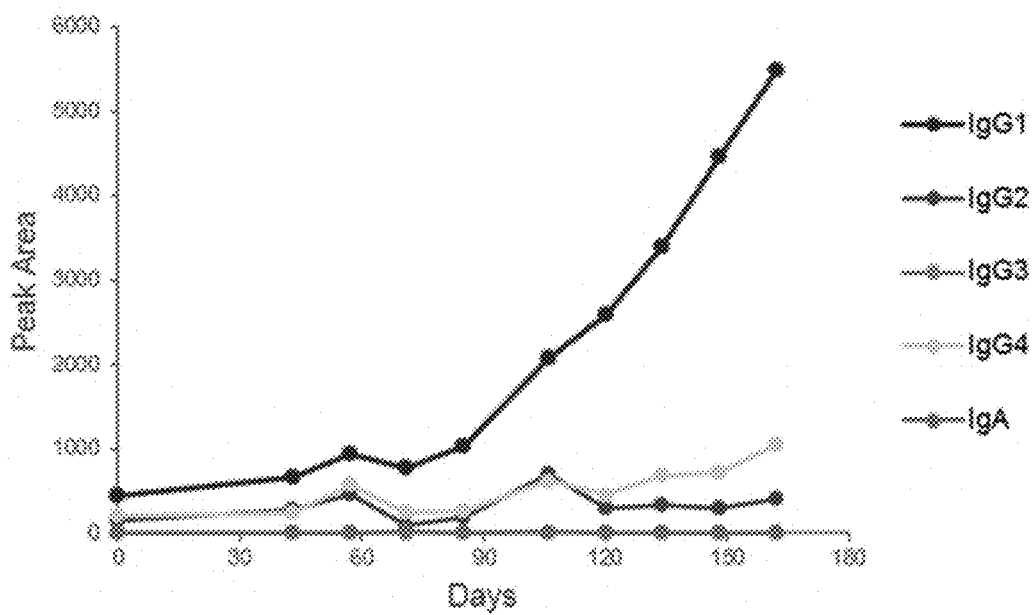

The serum samples of monkeys A and B were subjected to the isotyping and quantification of ADAs using the immunocapture-LC/MS methods of the present application. These methods were able to determine the relative quantifications of ADA isotypes including the quantities of IgG1, IgG2, IgG3, IgG4 and IgA, as shown in FIG. 17A for monkey A and as shown in FIG. 17B for monkey B.

Figure 18:
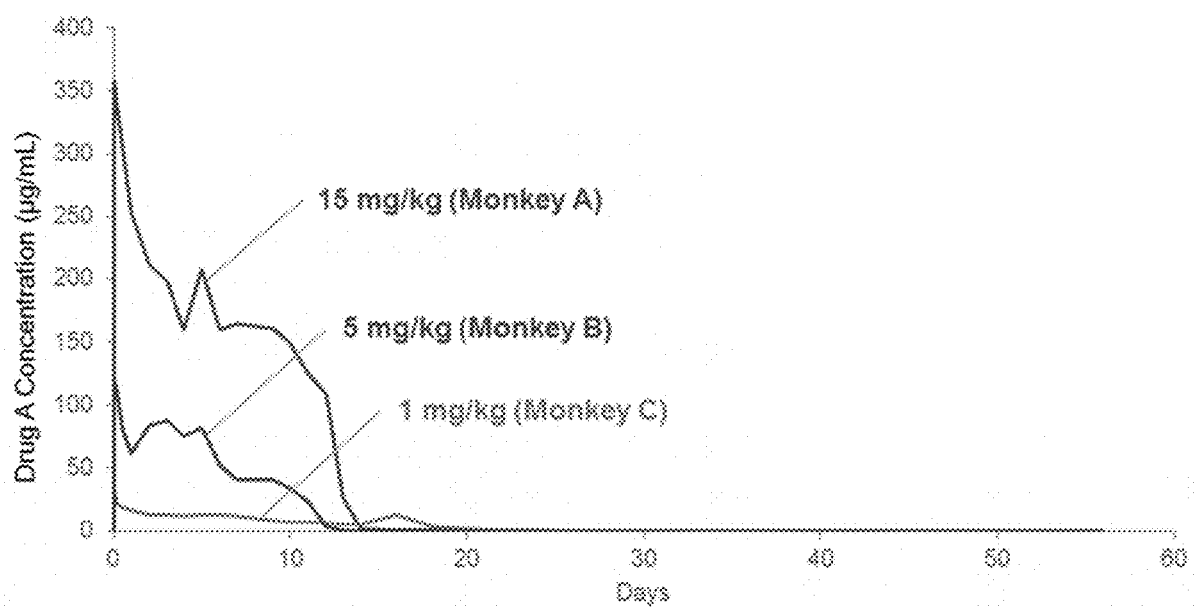
FIG. 18 shows the concentrations of drug A in the serum samples of monkeys A, B and C monitored over time in preclinical pharmacokinetic study for drug A according to an exemplary embodiment.
Figure 19:
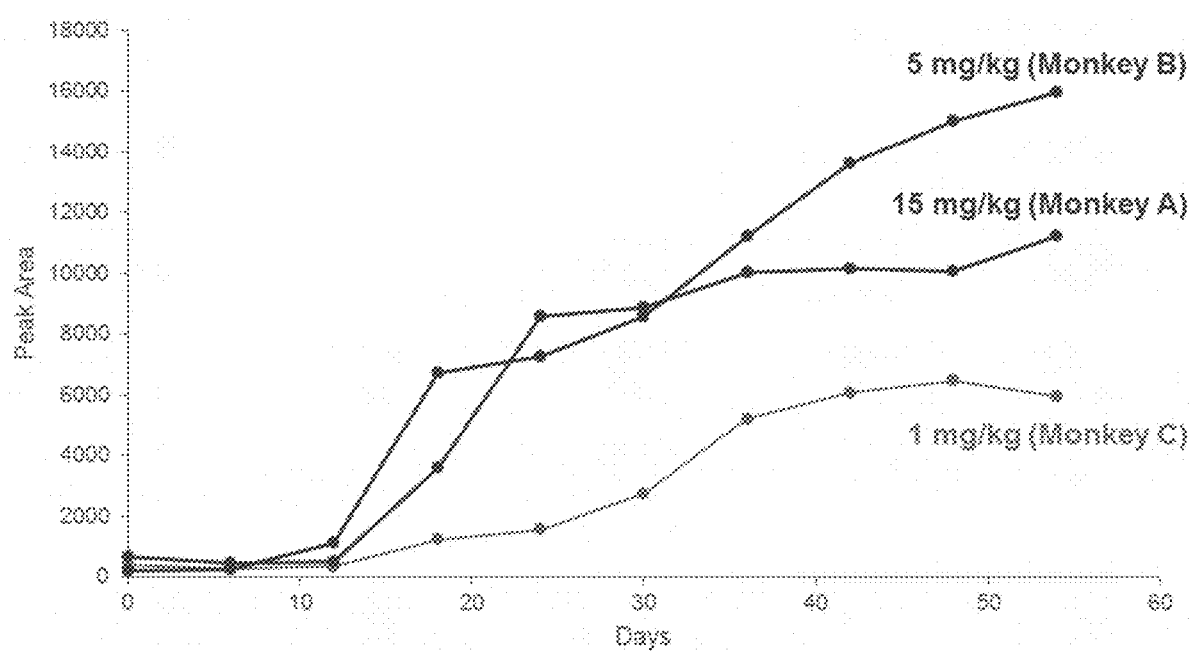
FIG. 19 shows the total quantities of ADAs in monkeys A, B and C measured by immunocapture-LC/MS methods of the present application for isotyping and quantification of ADAs in preclinical pharmacokinetic study in monkeys for drug A according to an exemplary embodiment.

Example 13. Isotyping and Quantification of ADAs in Preclinical Pharmacokinetic Study in Monkeys The immunocapture and LC-MS methods of the present application were used to isotype and quantify ADAs in preclinical pharmacokinetic study in monkeys for drug A. The monkeys were treated with drug A at single dose for the pharmacokinetic studies. Monkey A was treated at 15 mg/kg of drug A. Monkey B was treated with 5 mg/kg of drug A. Monkey C was treated with 1 mg/kg of drug A. The concentrations of drug A in the serum samples of monkeys A, B and C were monitored over time as shown in FIG. 18. The total quantities of ADAs in monkeys A, B and C were measured by immunocapture-LC/MS methods of the present application as shown in FIG. 19. The test results showed that the level of total ADAs was more subject dependent.

Figure 20:
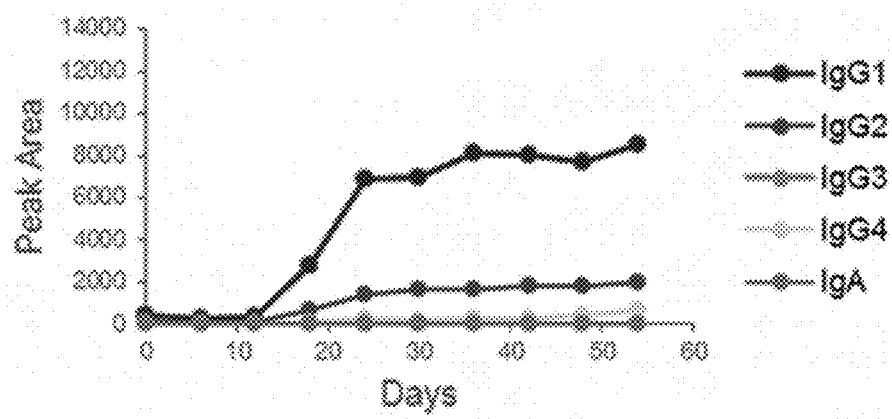
FIG. 20 shows relative quantifications of ADA isotypes including the quantities of IgG1, IgG2, IgG3, IgG4 and IgA in preclinical pharmacokinetic study in monkeys for drug A according to an exemplary embodiment.
Figure 20:
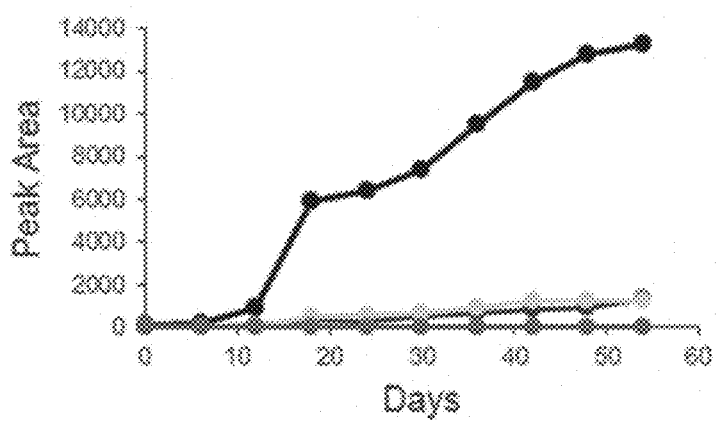
Figure 20:
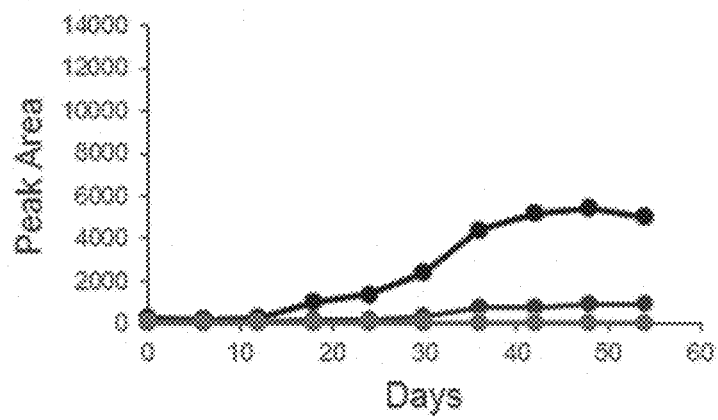

The serum samples of monkeys A, B and C were subjected to the isotyping and quantification of ADAs using the immunocapture-LC/MS methods of the present application. These methods were able to determine the relative quantifications of ADA isotypes including the quantities of IgG1, IgG2, IgG3, IgG4 and IgA, as shown in FIG. 20. The test results indicated that IgG1 subtype of ADAs contributed to the elevated levels of total ADAs in monkey B after 30 days.

What is claimed:

1. A method of identifying at least one peptide or protein in a sample, comprising:
   contacting the sample to a solid support, wherein at least one pharmaceutical product that is capable of interacting with the at least one peptide or protein has been attached to the solid support using a primary amine-epoxy reaction;
   washing the solid support using at least one mobile phase solution to provide at least one eluent;
   isolating the at least one peptide or protein from the eluent;
   treating the isolated peptide or protein with a denaturation solution and/or an enzymatic digestion reaction to generate components of the isolated peptide or protein;
   identifying the components of the isolated peptide or protein using a mass spectrometer.

2. The method of claim 1, wherein an isotype or subclass of the isolated peptide or protein is determined.

3. A method of claim 2, wherein the isolated peptide or protein is quantified using a mass spectrometer.

4. The method of claim 3, wherein the component of the isolated peptide or protein is at least about 0.01 ng, at least about 0.1 ng, at least about 0.2 ng, or at least about 0.3 ng.

5. The method of claim 3, wherein the method further comprises the steps of:
   conducting peptide mapping of the isolated peptide or protein,
   selecting unique peptides and fragment ions of the isolated peptide or protein to generate MRM (multiple reaction monitoring) transitions,
   selecting top two or top three transitions of the unique peptides,
   optimizing collision energy of the unique peptides,
   subsequently generating a calibration curve, and
   determining a LLOQ (lower limit of quantification) according to the calibration curve.

6. The method of claim 1, wherein the pharmaceutical product is a drug, a chemical compound, a nucleic acid, a toxin, a peptide, a protein, a fusion protein, an antibody, an antibody fragment, a Fab region of an antibody, an antibody-drug conjugate, or a protein pharmaceutical product.

7. The method of claim 1, wherein the at least one peptide or protein in the sample is an antibody that selectively binds to the pharmaceutical product attached to the solid support.

8. The method of claim 1, wherein the at least one peptide or protein in the sample is a human antibody, wherein an isotype of the human antibody is IgG1, IgG2, IgG3, IgG4, IgA1, IgA2, IgM, or IgE.

9. The method of claim 1, wherein the at least one peptide or protein in the sample is a mammalian antibody, wherein an isotype of the mammalian antibody is IgG1, IgG2, IgG3, IgG4, IgM, or IgA.

10. The method of claim 1, wherein the at least one peptide or protein in the sample is a human antibody, and wherein an amino acid sequence of the component of the isolated peptide or protein is GPSVFPLAPSSK (SEQ ID NO: 1), GLPAPIEK (SEQ ID NO: 2), WYVDGVEVHNAK (SEQ ID NO: 3), GLPSSIEK (SEQ ID NO: 4), DASGVTFTWTPSSGK (SEQ ID NO: 5), DASGATFTWTPSSGK (SEQ ID NO: 6), VSVFVPPR (SEQ ID NO: 7), or DFTPPTVK (SEQ ID NO: 8).

11. The method of claim 1, wherein the at least one peptide or protein in the sample is a mammalian antibody, wherein an amino acid sequence of the component of the isolated peptide or protein is GPSVFPLAPSSR (SEQ ID NO: 9), GPSVFPLASCSR (SEQ ID NO: 10), GPSVFPLVSCSR (SEQ ID NO: 11), GPSVFPLASSSR (SEQ ID NO: 12), QIEVSWLR (SEQ ID NO: 13), or DPSGATFTWTPSSGK (SEQ ID NO: 14).

12. The method of claim 1, wherein the sample is treated with a solution to reach a pH range of about 0.1-4.5 prior to contacting the solid support.

13. The method of claim 12, wherein the solution comprises acetic acid.

14. The method of claim 1, wherein the sample incubates with the solid support at room temperature for about 1 hour.

15. The method of claim 1, wherein the sample further comprises a salt and a surfactant.

16. The method of claim 1, wherein the sample further comprises BSA (bovine serum albumin), HEPES (4-(2-hydroxyethyl)-1-piperazineethanesulfonic acid), sodium chloride, EDTA (ethylenediaminetetraacetic acid) and Tween-20™ (polysorbate 20).

17. The method of claim 16, wherein the sample has a pH range of about 6-9.

18. The method of claim 1, wherein the solid support is washed using the at least one mobile phase solution that comprises a salt and a surfactant and at least another subsequent mobile phase solution that has a pH range of about 0.1 to 4.5.

19. The method of claim 18, wherein the at least one mobile phase solution comprises BSA (bovine serum albumin), HEPES (4-(2-hydroxyethyl)-1-piperazineethanesulfonic acid), sodium chloride, EDTA (ethylenediaminetetraacetic acid) and Tween-20™ (polysorbate 20) and has a pH range of about 6-9.

20. The method of claim 1, wherein the denaturation solution comprises about 5-10 M urea.

21. The method of claim 1, wherein an enzyme of the enzymatic digestion reaction is trypsin.

22. The method of claim 1, wherein the pharmaceutical product is attached to the solid support using a lysine residue of the pharmaceutical product.

23. The method of claim 1, wherein the mass spectrometer is an electrospray ionization mass spectrometer or nano-electrospray ionization mass spectrometer.

24. The method of claim 1, wherein the mass spectrometer is coupled to a liquid chromatography system.

25. The method of claim 1, wherein the mass spectrometer is capable of performing LC-MS (liquid chromatography-mass spectrometry) or a LC-MRM-MS (liquid chromatography-multiple reaction monitoring-mass spectrometry) analyses.

26. The method of claim 1, wherein the mass spectrometer is a triple quadrupole mass spectrometer.

27. A system for identifying or quantifying at least one peptide or protein in a sample, comprising:
a solid support, wherein a pharmaceutical product that is capable of interacting with the at least one peptide or protein has been attached to the solid support using a primary amine-epoxy reaction;
at least one mobile phase solution for washing the solid support and capable of providing at least one eluent containing the at least one peptide or protein for isolating the at least one peptide or protein;
a denaturation solution and/or an enzymatic digestion solution capable of generating components from the isolated peptide or protein; and
a mass spectrometer capable of identifying or quantifying the components from the isolated peptide or protein.

28. The system of claim 27, wherein the mass spectrometer is capable of identifying or quantifying an isotype or subclass of the isolated peptide or protein.

29. The system of claim 27, wherein the pharmaceutical product is a drug, a chemical compound, a nucleic acid, a toxin, a peptide, a protein, a fusion protein, an antibody, an antibody fragment, a Fab region of an antibody, an antibody-drug conjugate, or a protein pharmaceutical product.

30. The system of claim 27, wherein the at least one peptide or protein in the sample is an antibody that selectively binds to the pharmaceutical product attached to the solid support.

31. The system of claim 27, wherein the at least one peptide or protein in the sample is a human antibody, wherein an isotype of the human antibody is IgG1, IgG2, IgG3, IgG4, IgA1, IgA2, IgM, or IgE.

32. The system of claim 27, wherein the at least one peptide or protein in the sample is a mammalian antibody, wherein an isotype of the mammalian antibody is IgG1, IgG2, IgG3, IgG4, IgM, or IgA.

33. The system of claim 27, wherein the at least one peptide or protein in the sample is a human antibody, and wherein an amino acid sequence of the component of the isolated peptide or protein is GPSVFPLAPSSK (SEQ ID NO: 1), GLPAPIEK (SEQ ID NO: 2), WYVDGVEVHNAK (SEQ ID NO: 3), GLPSSIEK (SEQ ID NO: 4), DASGVTFTWTPSSGK (SEQ ID NO: 5), DASGATFTWTPSSGK (SEQ ID NO: 6), VSVFVPPR (SEQ ID NO: 7), or DFTPPTVK (SEQ ID NO: 8).

34. The system of claim 27, wherein the at least one peptide or protein in the sample is a mammalian antibody, wherein an amino acid sequence of the component of the isolated peptide or protein is GPSVFPLAPSSR (SEQ ID NO: 9), GPSVFPLASCSR (SEQ ID NO: 10), GPSVFPLVSCSR (SEQ ID NO: 11), GPSVFPLASSSR (SEQ ID NO: 12), QIEVSWLR (SEQ ID NO: 13), or DPSGATFTWTPSSGK (SEQ ID NO: 14).

35. The system of claim 27, wherein the sample is treated with a solution to reach a pH range of about 0.1-4.5 prior to contacting the solid support.

36. The system of claim 35, wherein the solution comprises acetic acid.

37. The system of claim 27, wherein the sample incubates on the solid support at room temperature for about 1 hour.

38. The system of claim 27, wherein the sample further comprises a salt and a surfactant.

39. The system of claim 27, wherein the sample further comprises BSA (bovine serum albumin), HEPES (4-(2-hydroxyethyl)-1-piperazineethanesulfonic acid), sodium chloride, EDTA (ethylenediaminetetraacetic acid) and Tween-20™ (polysorbate 20).

40. The system of claim 39, wherein the sample has a pH range of about 6-9.

41. The system of claim 27, wherein the solid support is washed using the at least one mobile phase solution that comprises a salt and a surfactant and at least another subsequent mobile phase solution that has a pH range of about 0.1 to 4.5.

42. The system of claim 41, wherein the at least one mobile phase solution comprises BSA (bovine serum albumin), HEPES (4-(2-hydroxyethyl)-1-piperazineethanesulfonic acid), sodium chloride, EDTA (ethylenediaminetetraacetic acid) and Tween-20™ (polysorbate 20) and has a pH range of about 6-9.

43. The system of claim 27, wherein the denaturation solution comprises about 5-10 M urea.

44. The system of claim 27, wherein an enzyme of the enzymatic digestion solution is trypsin.

45. The system of claim 27, wherein the pharmaceutical product is enclosed to the solid support using a lysine residue of the pharmaceutical product.

46. The system of claim 27, wherein the mass spectrometer is an electrospray ionization mass spectrometer or nano-electrospray ionization mass spectrometer.

47. The system of claim 27, wherein the mass spectrometer is coupled to a liquid chromatography system.

48. The system of claim 27, wherein the mass spectrometer is capable of performing LC-MS (liquid chromatography-mass spectrometry) or a LC-MRM-MS (liquid chromatography-multiple reaction monitoring-mass spectrometry) analyses.

49. The system of claim 27, wherein the mass spectrometer is a triple quadrupole mass spectrometer.

50. The system of claim 27, wherein the system is capable of:
conducting peptide mapping of the isolated peptide or protein,
selecting unique peptides and fragment ions of the isolated peptide or protein to generate MRM (multiple reaction monitoring) transitions,
selecting top two or top three transitions of the unique peptides,
optimizing collision energy of the unique peptides,
subsequently generating a calibration curve, and
determining a LLOQ (lower limit of quantification) according to the calibration curve.

* * * * *

UNITED STATES PATENT AND TRADEMARK OFFICE
CERTIFICATE OF CORRECTION

PATENT NO. : 12,411,141 B2
APPLICATION NO. : 17/022942
DATED : September 9, 2025
INVENTOR(S) : Xiaobin Xu et al.

Page 1 of 1

It is certified that error appears in the above-identified patent and that said Letters Patent is hereby corrected as shown below:

In the Claims

In Column 37, Line 38, Claim 3, delete "A" and insert --The--.
In Column 38, Lines 38-39, Claim 11, delete "GPSVFPLASSSR(SEQ ID NO: 12)," and insert --GPSVFPLASSSR (SEQ ID NO: 12),--.

Signed and Sealed this
Second Day of December, 2025

John A. Squires
*Director of the United States Patent and Trademark Office*